United States Patent
Marmur et al.

(10) Patent No.: US 12,201,510 B2
(45) Date of Patent: Jan. 21, 2025

(54) SELF-CURVING STENT-GRAFT

(71) Applicant: ENDOSPAN LTD., Herzilyia Pituach (IL)

(72) Inventors: Yaniv Marmur, Yokneam Moshava (IL); Tzachi Tziler, Modiin (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 281 days.

(21) Appl. No.: 16/774,683

(22) Filed: Jan. 28, 2020

(65) Prior Publication Data
US 2020/0155297 A1 May 21, 2020

Related U.S. Application Data

(63) Continuation of application No. 15/543,069, filed as application No. PCT/IL2016/050014 on Jan. 6, 2016, now abandoned.
(Continued)

(51) Int. Cl.
*A61F 2/07* (2013.01)

(52) U.S. Cl.
CPC ........ *A61F 2/07* (2013.01); *A61F 2210/0014* (2013.01); *A61F 2250/0006* (2013.01);
(Continued)

(58) Field of Classification Search
CPC .............. A61F 2/07; A61F 2250/0006; A61F 2250/0012; A61F 2250/0029
See application file for complete search history.

(56) References Cited

U.S. PATENT DOCUMENTS

| | | |
|---|---|---|
| 5,104,404 A | 4/1992 | Wolff |
| 5,755,781 A | 5/1998 | Jayaraman |
| (Continued) | | |

FOREIGN PATENT DOCUMENTS

| | | |
|---|---|---|
| AU | 2010201676 B1 | 7/2010 |
| CN | 2843384 Y | 12/2006 |
| (Continued) | | |

OTHER PUBLICATIONS

1st Office Action issued Chinese Appl. No. 201910460789.1, dated Nov. 19, 2020.
(Continued)

*Primary Examiner* — Christopher D. Prone
(74) *Attorney, Agent, or Firm* — Sughrue Mion, PLLC

(57) ABSTRACT

An endovascular stent-graft is provided, including a plurality of circumferential strut members disposed at respective axial positions along a self-curving longitudinal portion thereof. Each of the circumferential strut members is shaped so as to define a plurality of proximal peaks. When the stent-graft is unconstrained in a radially-expanded state, for at least one of the circumferential strut members, a first set of the proximal peaks of the circumferential strut member, which includes at least a circumferentially-closest one of the proximal peaks to an outermost curve of the self-curving longitudinal portion, are bent radially inward at least an average angle of 20 degrees toward a central longitudinal axis of the self-curving longitudinal portion, and a second set of the proximal peaks of the circumferential strut member are not bent radially inward by at least an average angle of 20 degrees toward the central longitudinal axis. Other embodiments are also described.

22 Claims, 7 Drawing Sheets

Related U.S. Application Data

(60) Provisional application No. 62/102,265, filed on Jan. 12, 2015.

(52) U.S. Cl.
CPC .................. *A61F 2250/0012* (2013.01); *A61F 2250/0029* (2013.01); *A61F 2250/0039* (2013.01)

(56) References Cited

U.S. PATENT DOCUMENTS

| | | | |
|---|---|---|---|
| 5,827,321 | A | 10/1998 | Roubin et al. |
| 5,855,600 | A | 1/1999 | Alt |
| 5,980,552 | A | 11/1999 | Pinchasik et al. |
| 6,036,725 | A | 3/2000 | Avellanet |
| 6,132,417 | A | 10/2000 | Kiesz |
| 6,270,524 | B1 | 8/2001 | Kim |
| 6,520,988 | B1 | 2/2003 | Colombo et al. |
| 7,279,003 | B2 | 10/2007 | Berra et al. |
| 7,625,400 | B2 * | 12/2009 | Bowe .................. A61F 2/91 623/1.11 |
| 7,708,704 | B2 | 5/2010 | Mitelberg et al. |
| 8,251,963 | B2 | 8/2012 | Chin et al. |
| 8,353,898 | B2 | 1/2013 | Lutze et al. |
| 8,425,585 | B2 | 4/2013 | Melsheimer et al. |
| 9,827,118 | B2 | 11/2017 | Hagaman et al. |
| 2001/0004705 | A1 | 6/2001 | Killion et al. |
| 2002/0013617 | A1 | 1/2002 | Matsutani et al. |
| 2002/0107564 | A1 | 8/2002 | Cox et al. |
| 2003/0088305 | A1 | 5/2003 | Van Schie et al. |
| 2003/0191523 | A1 | 10/2003 | Hojeibane |
| 2004/0106975 | A1 * | 6/2004 | Solovay .................. A61F 2/89 623/1.11 |
| 2004/0215319 | A1 | 10/2004 | Berra et al. |
| 2005/0177132 | A1 | 8/2005 | Lentz et al. |
| 2005/0216018 | A1 | 9/2005 | Sennett |
| 2005/0222667 | A1 | 10/2005 | Hunt |
| 2005/0240257 | A1 | 10/2005 | Ishimaru et al. |
| 2006/0173530 | A1 | 8/2006 | Das |
| 2007/0050011 | A1 | 3/2007 | Klein et al. |
| 2007/0167955 | A1 | 7/2007 | Arnault De La Menardiere et al. |
| 2007/0213807 | A1 | 9/2007 | Roubin et al. |
| 2007/0250154 | A1 | 10/2007 | Greenberg et al. |
| 2008/0195191 | A1 | 8/2008 | Luo et al. |
| 2009/0054967 | A1 | 2/2009 | Das |
| 2009/0069881 | A1 | 3/2009 | Chalekian et al. |
| 2009/0069882 | A1 | 3/2009 | Venturelli et al. |
| 2010/0249901 | A1 * | 9/2010 | Kang .................. A61F 2/91 623/1.15 |
| 2011/0125251 | A1 | 5/2011 | Cottone et al. |
| 2011/0208289 | A1 * | 8/2011 | Shalev .................. A61F 2/07 623/1.35 |
| 2011/0264192 | A1 | 10/2011 | Hartley et al. |
| 2012/0123464 | A1 | 5/2012 | Rasmussen et al. |
| 2012/0150274 | A1 | 6/2012 | Shalev et al. |
| 2012/0172965 | A1 | 7/2012 | Kratzberg et al. |
| 2012/0323305 | A1 | 12/2012 | Benary et al. |
| 2016/0030209 | A1 | 2/2016 | Shalev et al. |

FOREIGN PATENT DOCUMENTS

| | | |
|---|---|---|
| EP | 1177779 A2 | 2/2002 |
| WO | 1999/025273 A1 | 5/1999 |
| WO | 03/034948 A1 | 5/2003 |
| WO | 2008/107885 A2 | 9/2008 |
| WO | 2011/064782 A2 | 6/2011 |
| WO | 2011/100290 A1 | 8/2011 |
| WO | 2015/075708 A1 | 5/2015 |
| WO | 2016/098113 A1 | 6/2016 |
| WO | 2016/125137 A1 | 8/2016 |

OTHER PUBLICATIONS

Extended European Search Report dated Feb. 18, 2020, issued by the European Patent Office in application No. 19209770.7.

"Zenith TX2® TAA Endovascular Graft with Pro-Form™ and the Z-Trak® Plus Introduction System," Instruction for Use, Cook Medical, downloaded Dec. 23, 2014.

Pierce DS et al., "Open-cell vs. Closed-cell Stent Design Differences in Blood Flow Velocities after Carotid Stenting," J Vase Surg. Mar. 2009 ; 49(3): 602-606.

Lee WA et al., "First United States experience of the TX2 Pro-Form thoracic delivery system," J Vase Surg 52:1459-63 (2010).

An International Search Report and a Written Opinion both dated Jun. 21, 2016. which issued during the prosecution of Applicant's PCT/IL2016/050014.

* cited by examiner

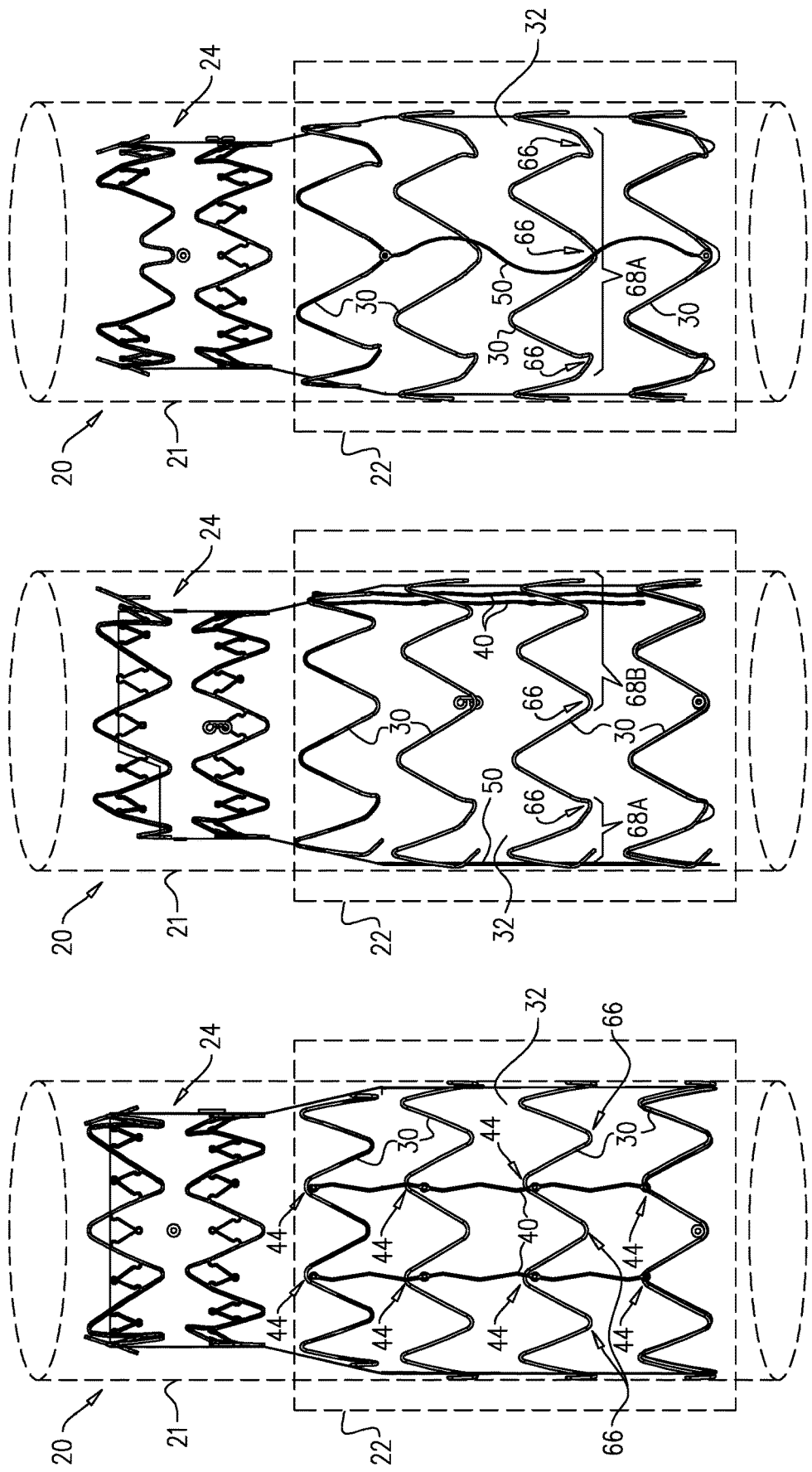

SELF-CURVING STENT-GRAFT

CROSS-REFERENCE TO RELATED APPLICATIONS

The present application is a continuation of U.S. application Ser. No. 15/543,069, filed Jul. 12, 2017, now abandoned, which is the U.S. national phase of PCT/IL2016/050014, filed Jan. 6, 2016, which claims priority from U.S. Provisional Application 62/102,265, filed Jan. 12, 2015, all of which applications are assigned to the assignee of the present application and are incorporated herein by reference.

FIELD OF THE APPLICATION

The present invention relates generally to implantable medical devices, and specifically to implantable stent-grafts.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms. A TAA may occur downstream the aortic arch, i.e., in the descending aorta. Alternatively, a TAA may occur in the aortic arch itself, where the aorta branches to supply the brachiocephalic, left carotid and subclavian arteries, or may occur in the ascending aorta.

Endo-Vascular Aneurysm Repair (EVAR) has transformed the practice of treatment of aortic aneurysms from an open surgical approach to a much less invasive surgical approach. The first step of an endovascular intervention usually requires introducing a delivery system into the vasculature of a subject. If the crossing profile, i.e., the external diameter, of the delivery system is 24 Fr or lower (3 Fr=1 millimeter), a true percutaneous approach may be used, because vascular closure devices are available for proper closure of such puncture sites.

Blood vessels occasionally weaken or even rupture. For example, in the aortic artery, the vascular wall can weaken or tear, resulting in dangerous conditions such as aneurysm and dissection. Treatment of such conditions can be performed by implanting a prosthesis within the vascular system using minimally-invasive surgical procedures. An endoluminal prosthesis typically includes one or more stents affixed to graft material and is delivered to the treatment site by endovascular insertion. Once the endoluminal prosthesis is radially enlarged, it should remain in place indefinitely by self-attachment to the vessel wall, acting as a substitute vessel for the flow of blood or other fluids.

Aortic dissection is a tear or partial tear in the inner wall of the aorta, which causes blood to flow between the layers of the wall of the aorta, forcing the layers apart. Aortic dissections may be divided into two types in accordance with the Stanford classification. Type A dissections involve the ascending aorta and/or aortic arch, and possibly the descending aorta. Type B dissections involve the descending aorta or the arch (distal to right brachiocephalic artery origin), without involvement of the ascending aorta.

When stent-grafts are deployed in curves in blood vessels, non-apposition of the stent-graft's edge, and especially the proximal (upstream) edge, with the tortuosity of the blood vessel may result, possibly leading to blood turbulence between the edge of the graft material and the vessel wall. Such blood turbulence may generate embolic debris, which may propagate downstream and create risk of embolism and organ damage. This problem is particularly common in the highly curved aortic arch and ascending aorta, in which non-apposition of the graft material with the lesser curve of the ascending aortic wall may occur and may generate emboli that could travel downstream to the brain. Such non-apposition is referred to as "bird-beaking" in the art, and may occur at either end of the stent-graft. Bird-beaking can also lead to device malperformance, such as type I endoleak, device migration, graft collapse, or stent fatigue, and/or release of embolic debris that may travel up to the supra-aortic vessels. FIG. 1 shows a prior-art stent-graft 10 implanted in an ascending aorta 12, with bird-beaking 14 occurring at both proximal and distal ends 16 and 18 of the stent-graft.

SUMMARY OF THE APPLICATION

In embodiments of the present invention, a generally tubular endovascular stent-graft comprises a self-curving longitudinal portion having proximal and distal ends. The stent-graft is configured to transition from a radially-compressed delivery state to a radially-expanded state. When the stent-graft is unconstrained in the radially-expanded state, the self-curving longitudinal portion of the stent-graft is curved so as to define an innermost curve and an outermost curve. The stent-graft comprises a plurality of circumferential strut members, disposed at respective axial positions along the self-curving longitudinal portion of the stent-graft, surrounding a central longitudinal axis of the self-curving longitudinal portion of the stent-graft. The stent-graft also comprises a graft member that is fixed to the circumferential strut members.

In order to curve the self-curving longitudinal portion, the stent-graft comprises:

a compression-generation spring, which (a) is in an elongated configuration when the stent-graft is in the radially-compressed state, and (b) overlaps respective first portions of at least two of the circumferential strut members; and an anti-buckling spring, which (a) is in a substantially relaxed or longitudinally-compressed configuration when the stent-graft is in the radially-compressed state, and (b) overlaps respective second portions of at least two of the circumferential strut members.

The anti-buckling spring and the compression-generation spring are together configured to curve the self-curving longitudinal portion of the stent-graft when the stent-graft is unconstrained in the radially-expanded state, such that:

a lesser length of the self-curving longitudinal portion of the stent-graft, measured along the innermost curve, is less than 80% (e.g., less than 75%) of a greater length of the self-curving longitudinal portion of the stent-graft, measured along the outermost curve, and/or (a) a proximal-most third of the self-curving longitudinal portion, measured along the central longitudinal axis of the self-curving longitudinal portion, has proximal-most and distal-most center points on the central longitudinal axis, which points together define a proximal-third straight line, (b) a distal-most third of the self-curving longitudinal portion, measured along the central longitudinal axis of the self-curving longitudinal portion, has proximal-most and distal-most center points on the central longitudinal axis, which points together define a distal-third straight line, and (c) a tilt angle between (a) the proximal-third straight line and (b) the distal-third straight line is at least 20 degrees.

Because of the self-curving longitudinal portion, the stent-graft is suitable for highly curved blood vessels, and especially those that are directly proximal to the brain and visceral organs, such as the ascending aorta and the aortic arch. The self-curving longitudinal portion causes apposition of the stent-graft to the vessel wall, thereby preventing the "bird-beaking" phenomenon, as explained hereinabove.

For some applications, an angle about the central longitudinal axis of the self-curving longitudinal portion of the stent-graft between the anti-buckling spring and the compression-generation spring, averaged along the self-curving longitudinal portion of the stent-graft, is between 140 and 220 degrees, such as between 160 and 200 degrees, when stent-graft 20 is unconstrained in the radially-expanded state.

The stent-graft is typically deployed in a transvascular (typically percutaneous) procedure. The stent-graft is positioned at the desired anatomical site, with at least the self-curving longitudinal portion in a curved portion of the blood vessel. If necessary, the stent-graft is rotated, typically before deployment from a delivery tube, such that:
  the compression-generation spring is circumferentially aligned with a lesser curve of the ascending aorta, and
  the anti-buckling spring is circumferentially aligned with a greater curve of the ascending aorta.

The curvature that the self-curving longitudinal portion of the stent-graft assumes upon deployment creates a tight seal between the graft member at both the proximal and the distal ends of the self-curving longitudinal portion and the lesser curve of the ascending aorta, thereby preventing bird-beaking.

There is therefore provided, in accordance with an application of the present invention, apparatus including a generally tubular endovascular self-curving stent-graft, which (a) includes a self-curving longitudinal portion having proximal and distal ends, (b) is configured to transition from a radially-compressed delivery state to a radially-expanded state, wherein, when the stent-graft is unconstrained in the radially-expanded state, the self-curving longitudinal portion of the stent-graft is curved so as to define an innermost curve and an outermost curve, and (c) includes:
  a plurality of circumferential strut members, disposed at respective axial positions along the self-curving longitudinal portion of the stent-graft, surrounding a central longitudinal axis of the self-curving longitudinal portion of the stent-graft;
  a graft member, which includes one or more substantially blood-impervious flexible sheets, and which is fixed to the circumferential strut members;
  a compression-generation spring, which (a) is in an elongated configuration when the stent-graft is in the radially-compressed state, and (b) overlaps respective first portions of at least two of the circumferential strut members; and
  an anti-buckling spring, which overlaps respective second portions of at least two of the circumferential strut members,
  wherein the anti-buckling spring and the compression-generation spring are together configured to curve the self-curving longitudinal portion of the stent-graft when the stent-graft is unconstrained in the radially-expanded state, such that a lesser length of the self-curving longitudinal portion of the stent-graft, measured along the innermost curve, is less than 80% of a greater length of the self-curving longitudinal portion of the stent-graft, measured along the outermost curve.

For some applications, the anti-buckling spring and the compression-generation spring are together configured such that when the stent-graft is unconstrained in the radially-expanded state:
  a proximal-most third of the self-curving longitudinal portion, measured along the central longitudinal axis of the self-curving longitudinal portion, has proximal-most and distal-most center points on the central longitudinal axis, which points together define a proximal-third straight line,
  a distal-most third of the self-curving longitudinal portion, measured along the central longitudinal axis of the self-curving longitudinal portion, has proximal-most and distal-most center points on the central longitudinal axis, which points together define a distal-third straight line,
  a tilt angle between (a) the proximal-third straight line and (b) the distal-third straight line is at least 20 degrees.

For some applications, the tilt angle is at least 30 degrees, such as at least 45 degrees, when the stent-graft is unconstrained in the radially-expanded state.

For some applications, if the stent-graft were to be placed in a right circular cylinder while in the radially-expanded state, the compression-generation spring would be substantially longitudinally-disposed. For some applications, if the stent-graft were to be placed in a right circular cylinder while in the radially-expanded state, the anti-buckling spring would be substantially longitudinally-disposed. For some applications, if the stent-graft were to be placed in a right circular cylinder while in the radially-expanded state, each of the compression-generation spring and the anti-buckling spring would be substantially longitudinally-disposed.

For some applications, the anti-buckling spring and the compression-generation spring are together configured such that when the stent-graft is unconstrained in the radially-expanded state, a second tilt angle between (a) a central longitudinal axis of a proximal-most one of the circumferential strut members and (b) a central longitudinal axis of a distal-most one of the circumferential strut members is at least 20 degrees, such as at least 30 degrees, e.g., at least 45 degrees.

For some applications, the anti-buckling spring and the compression-generation spring are together configured such that, when the stent-graft is unconstrained in the radially-expanded state, the lesser length of the self-curving longitudinal portion of the stent-graft is less than 75% of the greater length of the self-curving longitudinal portion of the stent-graft.

For some applications, a length of the compression-generation spring is at least 15% greater, e.g., at least 20% greater, when the stent-graft is in the radially-compressed delivery state than when the stent-graft is unconstrained in the radially-expanded state.

For some applications, a length of the anti-buckling spring is no more than 10% greater, e.g., no more than 5% greater, when the stent-graft is in the radially-compressed delivery state than when the stent-graft is unconstrained in the radially-expanded state.

For some applications, the self-curving longitudinal portion of the stent-graft longitudinally extends along 100% of the stent-graft.

For some applications, a height of each of the circumferential strut members of the self-curving longitudinal portion of the stent-graft, measured along the stent-graft, is greater at the outermost curve than at the innermost curve, when the stent-graft is unconstrained in the radially-expanded state.

For some applications, the anti-buckling spring includes exactly one structural strut element. For some applications, the compression-generation spring includes exactly one structural strut element.

For some applications, the anti-buckling spring is in a substantially relaxed configuration when the stent-graft is unconstrained in the radially-expanded state.

For some applications, the anti-buckling spring is in a longitudinally-compressed configuration when the stent-graft is unconstrained in the radially-expanded state.

For some applications, the compression-generation spring is fixed to the respective first portions of the at least two of the circumferential strut members.

For some applications, the anti-buckling spring is fixed to the respective second portions of the at least two of the circumferential strut members.

For some applications, the compression-generation spring is fixed to the graft member at a plurality of locations on the graft member.

For some applications, the anti-buckling spring is fixed to the graft member at a plurality of locations on the graft member.

For some applications, the compression-generation spring is fixed to (a) the respective first portions of the at least two of the circumferential strut members, and (b) the graft member at a plurality of locations on the graft member.

For some applications, the anti-buckling spring is fixed to (a) the respective second portions of the at least two of the circumferential strut members, and (b) the graft member at a plurality of locations on the graft member.

For some applications, the compression-generation spring overlaps respective first portions of at least three of the circumferential strut members. For some applications, the anti-buckling spring overlaps respective second portions of at least three of the circumferential strut members.

For some applications, a longitudinal spring constant of the compression-generation spring is 70 N/m to 300 N/m. For some applications, a longitudinal spring constant of the anti-buckling spring is 70 N/m to 300 N/m.

For some applications, if the stent-graft were to be placed in a right circular cylinder while in the radially-expanded state, an axial compression force exerted by the compression-generation spring against an inner surface of the cylinder would be 3 to 10 N.

For some applications, the stent-graft further includes a distal straight portion, when the stent-graft is unconstrained in the radially-expanded state.

For some applications, the anti-buckling spring and the compression-generation spring are together configured such that when the stent-graft is unconstrained in the radially-expanded state:
 a proximal-most third of the self-curving longitudinal portion, measured along the central longitudinal axis of the self-curving longitudinal portion, has proximal-most and distal-most center points on the central longitudinal axis, which points together define a proximal-third straight line, and
 an angle between (a) the proximal-third straight line and (b) a straight central longitudinal axis of the distal straight portion is at least 20 degrees.

For some applications, when the stent-graft is in unconstrained in the radially-expanded state, a minimum length of the self-curving longitudinal portion of the stent-graft, measured along the innermost curve of the self-curving longitudinal portion of the stent-graft, is at least 15% less than a centerline length of the self-curving longitudinal portion of the stent-graft, measured along the central longitudinal axis of the self-curving longitudinal portion of the stent-graft.

For some applications, when the stent-graft is in unconstrained in the radially-expanded state, a maximum length of the self-curving longitudinal portion of the stent-graft, measured along the outermost curve of the self-curving longitudinal portion of the stent-graft, is at least 15% greater than a centerline length of the self-curving longitudinal portion of the stent-graft, measured along the central longitudinal axis of the self-curving longitudinal portion of the stent-graft.

For some applications, an average radius of curvature of the outermost curve equals at least 120% of an average radius of curvature of the innermost curve, both average radii of curvature being measured along the self-curving longitudinal portion when the stent-graft is unconstrained in the radially-expanded state.

For some applications:
 each of the circumferential strut members of the self-curving longitudinal portion is shaped so as to define a plurality of proximal peaks, and
 when the stent-graft is unconstrained in the radially-expanded state, for at least one of the circumferential strut members of the self-curving longitudinal portion:
  a first set of the proximal peaks of the circumferential strut member, which includes at least a circumferentially-closest one of the proximal peaks to the outermost curve of the self-curving longitudinal portion, and no more than half of the proximal peaks of the circumferential strut member, are bent radially inward at least an average angle of 20 degrees toward the central longitudinal axis of the self-curving longitudinal portion, and
  a second set of the proximal peaks of the circumferential strut member, which includes all of the proximal peaks of the circumferential strut member not in the first set, are not bent radially inward by at least an average angle of 20 degrees toward the central longitudinal axis of the self-curving longitudinal portion.

For some applications, an average circumference the self-curving longitudinal portion of the stent-graft is between 9 and 16 cm, when the stent-graft is unconstrained in the radially-expanded state.

For some applications, a length of the self-curving longitudinal portion of the stent-graft, measured along the central longitudinal axis of the self-curving longitudinal portion of the stent-graft, is between 4 and 10 cm, when the stent-graft is unconstrained in the radially-expanded state.

For some applications, the one or more blood-impervious flexible sheets include polyethylene terephthalate. For some applications, the one or more blood-impervious flexible sheets include expanded PTFE. For some applications, the circumferential strut members, the compression-generation spring, and the anti-buckling spring include a flexible metal. For some applications, the metal includes a super-elastic alloy. For some applications, the alloy includes Nitinol.

For some applications, the apparatus further includes an elongate delivery tube, in which the stent-graft is removably disposed while in the radially-compressed delivery state, and a ratio of (a) an average circumference of the stent-graft when in the radially-expanded state to (b) an inner circumference of the elongate delivery tube is at least 7.

For some applications, an angle about the central longitudinal axis of the self-curving longitudinal portion of the stent-graft between the anti-buckling spring and the compression-generation spring, averaged along the self-curving longitudinal portion of the stent-graft, is between 140 and 220 degrees, when the stent-graft is unconstrained in the radially-expanded state.

For some applications, the angle is between 160 and 200 degrees.

For some applications, the stent-graft includes a plurality of anti-buckling springs.

For some applications, respective average circumferential angles about the central longitudinal axis of the self-curving longitudinal portion of the stent-graft between the anti-buckling springs and the compression-generation spring, averaged along the self-curving longitudinal portion of the stent-graft, are between 140 and 220 degrees, when the stent-graft is unconstrained in the radially-expanded state.

For some applications, the respective average circumferential angles are between 160 and 200 degrees.

For some applications, when the stent-graft is unconstrained in the radially-expanded state:
the anti-buckling springs are disposed at an average circumferential location about the central longitudinal axis of the self-curving longitudinal portion of the stent-graft, and
an angle about the central longitudinal axis of the self-curving longitudinal portion of the stent-graft between the average circumferential location and the compression-generation spring, averaged along the self-curving longitudinal portion of the stent-graft, is between 140 and 220 degrees.

For some applications, the angle is between 160 and 200 degrees.

For some applications, a collective longitudinal spring constant of the anti-buckling springs in combination is 70 N/m to 300 N/m.

For some applications, the stent-graft includes a plurality of compression-generation springs.

For some applications, respective average circumferential angles about the central longitudinal axis of the self-curving longitudinal portion of the stent-graft between the anti-buckling spring and the compression-generation springs, averaged along the self-curving longitudinal portion of the stent-graft, are between 140 and 220 degrees, when the stent-graft is unconstrained in the radially-expanded state.

For some applications, the respective average circumferential angles are between 160 and 200 degrees.

For some applications, when the stent-graft is unconstrained in the radially-expanded state:
the compression-generation springs are disposed at an average circumferential location about the central longitudinal axis of the self-curving longitudinal portion of the stent-graft, and
an angle about the central longitudinal axis of the self-curving longitudinal portion of the stent-graft between the average circumferential location and the anti-buckling spring, averaged along the self-curving longitudinal portion of the stent-graft, is between 140 and 220 degrees, such as between 160 and 200 degrees.

For some applications, a collective longitudinal spring constant of the compression-generation springs in combination is 70 N/m to 300) N/m.

There is further provided, in accordance with an application of the present invention, apparatus including a generally tubular endovascular self-curving stent-graft, which (a) includes a self-curving longitudinal portion having proximal and distal ends, (b) is configured to transition from a radially-compressed delivery state to a radially-expanded state, wherein, when the stent-graft is unconstrained in the radially-expanded state, the self-curving longitudinal portion of the stent-graft is curved so as to define an innermost curve and an outermost curve, and (c) includes:
a plurality of circumferential strut members, disposed at respective axial positions along the self-curving longitudinal portion of the stent-graft, surrounding a central longitudinal axis of the self-curving longitudinal portion of the stent-graft;
a graft member, which includes one or more substantially blood-impervious flexible sheets, and which is fixed to the circumferential strut members;
a compression-generation spring, which (a) is in an elongated configuration when the stent-graft is in the radially-compressed state, and (b) overlaps respective first portions of at least two of the circumferential strut members; and
an anti-buckling spring, which overlaps respective second portions of at least two of the circumferential strut members,
wherein the anti-buckling spring and the compression-generation spring are together configured to curve the self-curving longitudinal portion of the stent-graft when the stent-graft is unconstrained in the radially-expanded state, such that:
a proximal-most third of the self-curving longitudinal portion, measured along the central longitudinal axis of the self-curving longitudinal portion, has proximal-most and distal-most center points on the central longitudinal axis, which points together define a proximal-third straight line,
a distal-most third of the self-curving longitudinal portion, measured along the central longitudinal axis of the self-curving longitudinal portion, has proximal-most and distal-most center points on the central longitudinal axis, which points together define a distal-third straight line,
a tilt angle between (a) the proximal-third straight line and (b) the distal-third straight line is at least 20 degrees, such as at least 30 degrees, e.g., at least 45 degrees.

For some applications, the stent-graft further includes a distal straight portion, when the stent-graft is unconstrained in the radially-expanded state.

For some applications, the anti-buckling spring and the compression-generation spring are together configured such that when the stent-graft is unconstrained in the radially-expanded state, an angle between (a) the proximal-third straight line and (b) a straight central longitudinal axis of the distal straight portion is at least 20 degrees.

There is further provided, in accordance with an application of the present invention, apparatus including a generally tubular endovascular self-curving stent-graft, which (a) includes a self-curving longitudinal portion having proximal and distal ends, (b) is configured to transition from a radially-compressed delivery state to a radially-expanded state, wherein, when the stent-graft is unconstrained in the radially-expanded state, the self-curving longitudinal portion of the stent-graft is curved so as to define an innermost curve and an outermost curve, and (c) includes:
a plurality of circumferential strut members, disposed at respective axial positions along the self-curving longitudinal portion of the stent-graft, surrounding a central longitudinal axis of the self-curving longitudinal portion of the stent-graft;

a graft member, which includes one or more substantially blood-impervious flexible sheets, and which is fixed to the circumferential strut members;

a compression-generation spring, which (a) is in an elongated configuration when the stent-graft is in the radially-compressed state, and (b) overlaps respective first portions of at least two of the circumferential strut members; and an anti-buckling spring, which overlaps respective second portions of at least two of the circumferential strut members, wherein the anti-buckling spring and the compression-generation spring are together configured to curve the self-curving longitudinal portion of the stent-graft when the stent-graft is unconstrained in the radially-expanded state, such that a tilt angle between (a) a central longitudinal axis of a proximal-most one of the circumferential strut members and (b) a central longitudinal axis of a distal-most one of the circumferential strut members is at least 20 degrees, such as at least 30 degrees, e.g., at least 45 degrees.

For some applications, the stent-graft further includes a distal straight portion, when the stent-graft is unconstrained in the radially-expanded state.

For some applications, the anti-buckling spring and the compression-generation spring are together configured such that when the stent-graft is unconstrained in the radially-expanded state, an angle between (a) the central longitudinal axis of the proximal-most one of the circumferential strut members and (b) a straight central longitudinal axis of the distal straight portion is at least 20 degrees.

There is further provided, in accordance with an application of the present invention, apparatus including a generally tubular endovascular self-curving stent-graft, which (a) includes a self-curving longitudinal portion having proximal and distal ends, (b) is configured to transition from a radially-compressed delivery state to a radially-expanded state, wherein, when the stent-graft is unconstrained in the radially-expanded state, the self-curving longitudinal portion of the stent-graft is curved so as to define an innermost curve and an outermost curve, and (c) includes:

a plurality of circumferential strut members, disposed at respective axial positions along the self-curving longitudinal portion of the stent-graft, surrounding a central longitudinal axis of the self-curving longitudinal portion of the stent-graft, wherein each of the circumferential strut members of the self-curving longitudinal portion is shaped so as to define a plurality of proximal peaks; and a graft member, which includes one or more substantially blood-impervious flexible sheets, and which is fixed to the circumferential strut members, wherein, when the stent-graft is unconstrained in the radially-expanded state, for at least one of the circumferential strut members of the self-curving longitudinal portion:

a first set of the proximal peaks of the circumferential strut member, which includes at least a circumferentially-closest one of the proximal peaks to the outermost curve of the self-curving longitudinal portion, and no more than half of the proximal peaks of the circumferential strut member, are bent radially inward at least an average angle of 20 degrees toward the central longitudinal axis of the self-curving longitudinal portion, and a second set of the proximal peaks of the circumferential strut member, which includes all of the proximal peaks of the circumferential strut member not in the first set, are not bent radially inward by at least an average angle of 20 degrees toward the central longitudinal axis of the self-curving longitudinal portion.

There is further provided, in accordance with an application of the present invention, a method for treating a subject, including:

transvascularly introducing a generally tubular endovascular self-curving stent-graft into a blood vessel of the subject while the stent-graft is in a radially-compressed delivery state, which stent-graft (1) includes a self-curving longitudinal portion having proximal and distal ends, (2) is configured to transition from the radially-compressed delivery state to a radially-expanded state, wherein, when the stent-graft is unconstrained in the radially-expanded state, the self-curving longitudinal portion of the stent-graft is curved so as to define an innermost curve and an outermost curve, and (3) includes:

(i) a plurality of circumferential strut members, disposed at respective axial positions along the self-curving longitudinal portion of the stent-graft, surrounding a central longitudinal axis of the self-curving longitudinal portion of the stent-graft;

(ii) a graft member, which includes one or more substantially blood-impervious flexible sheets, and which is fixed to the circumferential strut members;

(iii) a compression-generation spring, which (a) is in an elongated configuration when the stent-graft is in the radially-compressed state, and (b) overlaps respective first portions of at least two of the circumferential strut members; and (iv) an anti-buckling spring, which overlaps respective second portions of at least two of the circumferential strut members, wherein the anti-buckling spring and the compression-generation spring are together configured to curve the self-curving longitudinal portion of the stent-graft when the stent-graft is unconstrained in the radially-expanded stale, such that (A) a lesser length of the self-curving longitudinal portion of the stent-graft, measured along the innermost curve, is less than 80% of a greater length of the self-curving longitudinal portion of the stent-graft, measured along the outermost curve; and creating a tight seal between the graft member at the proximal end of the self-curving longitudinal portion of the stent-graft and a wall of the curved blood vessel, by transitioning the stent-graft to the radially-expanded state in the curved blood vessel.

For some applications, the anti-buckling spring and the compression-generation spring are together configured such that when the stent-graft is unconstrained in the radially-expanded state:

a proximal-most third of the self-curving longitudinal portion, measured along the central longitudinal axis of the self-curving longitudinal portion, has proximal-most and distal-most center points on the central longitudinal axis, which points together define a proximal-third straight line, a distal-most third of the self-curving longitudinal portion, measured along the central longitudinal axis of the self-curving longitudinal portion, has proximal-most and distal-most center points on the central longitudinal axis, which points together define a distal-third straight line, a tilt angle between (a) the proximal-third straight line and (b) the distal-third straight line is at least 20 degrees, such as at least 30 degrees, e.g., at least 45 degrees.

For some applications, if the stent-graft were to be placed in a right circular cylinder while in the radially-expanded state, the compression-generation spring would be substantially longitudinally-disposed.

For some applications, if the stent-graft were to be placed in a right circular cylinder while in the radially-expanded state, the anti-buckling spring would be substantially longitudinally-disposed.

For some applications, if the stent-graft were to be placed in a right circular cylinder while in the radially-expanded state, each of the compression-generation spring and the anti-buckling spring would be substantially longitudinally-disposed.

For some applications, the anti-buckling spring and the compression-generation spring are together configured such that when the stent-graft is unconstrained in the radially-expanded state, a second tilt angle between (a) a central longitudinal axis of a proximal-most one of the circumferential strut members and (b) a central longitudinal axis of a distal-most one of the circumferential strut members is at least 20 degrees, such as at least 30 degrees, e.g., at least 45 degrees.

For some applications, the curved blood vessel is an aorta. For some applications, the aorta is pathologically dilated.

For some applications, the method further includes circumferentially aligning the compression-generation spring with a lesser curve of an ascending aorta, and the anti-buckling spring with a greater curve of the ascending aorta.

For some applications, the method further includes circumferentially aligning the compression-generation spring with a lesser curve of the curved blood vessel, and the anti-buckling spring with a greater curve of the curved blood vessel.

For some applications, transvascularly introducing the stent-graft includes:
  assessing a curvature of the curved blood vessel; and
  responsively to the assessed curvature, selecting the self-curving stent-graft from a plurality of self-curving stent-grafts having different respective radii of curvature.

For some applications, transvascularly introducing the stent-graft includes:
  assessing a curvature and diameter of the curved blood vessel; and
  responsively to the assessed curvature and diameter, selecting the self-curving stent-graft from a plurality of self-curving stent-grafts having different respective combinations of radii of curvature, diameters, and treatable lengths.

For some applications, transvascularly introducing the stent-graft includes:
  assessing a radius of curvature of a lesser curve of the curved blood vessel; and
  selecting the self-curving stent-graft from a plurality of self-curving stent-grafts having innermost curves with different respective radii of curvature, such that the selected self-curving stent-graft has a radius of curvature of the innermost curve that is less than the radius of curvature of the lesser curve of the curved blood vessel.

For some applications, the anti-buckling spring and the compression-generation spring are together configured such that, when the stent-graft is unconstrained in the radially-expanded state, the lesser length of the self-curving longitudinal portion of the stent-graft is less than 75% of the greater length of the self-curving longitudinal portion of the stent-graft.

For some applications, a length of the compression-generation spring is at least 15% greater, e.g., at least 20% greater, when the stent-graft is in the radially-compressed delivery state than when the stent-graft is unconstrained in the radially-expanded state.

For some applications, a length of the anti-buckling spring is no more than 10% greater, e.g., no more than 5% greater, when the stent-graft is in the radially-compressed delivery state than when the stent-graft is unconstrained in the radially-expanded state.

For some applications, the self-curving longitudinal portion of the stent-graft longitudinally extends along 100% of the stent-graft.

For some applications, a height of each of the circumferential strut members of the self-curving longitudinal portion of the stent-graft, measured along the stent-graft, is greater at the outermost curve than at the innermost curve, when the stent-graft is unconstrained in the radially-expanded state.

For some applications, the anti-buckling spring includes exactly one structural strut element.

For some applications, the compression-generation spring includes exactly one structural strut element.

For some applications, the anti-buckling spring is in a substantially relaxed configuration when the stent-graft is unconstrained in the radially-expanded state.

For some applications, the anti-buckling spring is in a longitudinally-compressed configuration when the stent-graft is unconstrained in the radially-expanded state.

For some applications, the compression-generation spring is fixed to the respective first portions of the at least two of the circumferential strut members.

For some applications, the anti-buckling spring is fixed to the respective second portions of the at least two of the circumferential strut members.

For some applications, the compression-generation spring is fixed to the graft member at a plurality of locations on the graft member.

For some applications, the anti-buckling spring is fixed to the graft member at a plurality of locations on the graft member.

For some applications, the compression-generation spring is fixed to (a) the respective first portions of the at least two of the circumferential strut members, and (b) the graft member at a plurality of locations on the graft member.

For some applications, the anti-buckling spring is fixed to (a) the respective second portions of the at least two of the circumferential strut members, and (b) the graft member at a plurality of locations on the graft member.

For some applications, the compression-generation spring overlaps respective first portions of at least three of the circumferential strut members.

For some applications, the anti-buckling spring overlaps respective second portions of at least three of the circumferential strut members.

For some applications, a longitudinal spring constant of the compression-generation spring is 70 N/m to 300 N/m.

For some applications, a longitudinal spring constant of the anti-buckling spring is 70 N/m to 300 N/m.

For some applications, if the stent-graft were to be placed in a right circular cylinder while in the radially-expanded state, an axial compression force exerted by the compression-generation spring against an inner surface of the cylinder would be 3 to 10 N.

For some applications, the stent-graft further includes a distal straight portion, when the stent-graft is unconstrained in the radially-expanded state.

For some applications, the anti-buckling spring and the compression-generation spring are together configured such that when the stent-graft is unconstrained in the radially-expanded state:
  a proximal-most third of the self-curving longitudinal portion, measured along the central longitudinal axis of the self-curving longitudinal portion, has proximal-most and distal-most center points on the central longitudinal axis, which points together define a proximal-third straight line, and
  an angle between (a) the proximal-third straight line and (b) a straight central longitudinal axis of the distal straight portion is at least 20 degrees.

For some applications, when the stent-graft is in unconstrained in the radially-expanded state, a minimum length of the self-curving longitudinal portion of the stent-graft, measured along the innermost curve of the self-curving longitudinal portion of the stent-graft, is at least 15% less than a centerline length of the self-curving longitudinal portion of the stent-graft, measured along the central longitudinal axis of the self-curving longitudinal portion of the stent-graft.

For some applications, when the stent-graft is in unconstrained in the radially-expanded state, a maximum length of the self-curving longitudinal portion of the stent-graft, measured along the outermost curve of the self-curving longitudinal portion of the stent-graft, is at least 15% greater than a centerline length of the self-curving longitudinal portion of the stent-graft, measured along the central longitudinal axis of the self-curving longitudinal portion of the stent-graft.

For some applications, an average radius of curvature of the outermost curve equals at least 120% of an average radius of curvature of the innermost curve, both average radii of curvature being measured along the self-curving longitudinal portion when the stent-graft is unconstrained in the radially-expanded state.

For some applications:
  each of the circumferential strut members of the self-curving longitudinal portion is shaped so as to define a plurality of proximal peaks, and
  when the stent-graft is unconstrained in the radially-expanded state, for at least one of the circumferential strut members of the self-curving longitudinal portion:
    a first set of the proximal peaks of the circumferential strut member, which includes at least a circumferentially-closest one of the proximal peaks to the outermost curve of the self-curving longitudinal portion, and no more than half of the proximal peaks of the circumferential strut member, are bent radially inward at least an average angle of 20 degrees toward the central longitudinal axis of the self-curving longitudinal portion, and
    a second set of the proximal peaks of the circumferential strut member, which includes all of the proximal peaks of the circumferential strut member not in the first set, are not bent radially inward by at least an average angle of 20 degrees toward the central longitudinal axis of the self-curving longitudinal portion.

For some applications, an average circumference the self-curving longitudinal portion of the stent-graft is between 9 and 16 cm, when the stent-graft is unconstrained in the radially-expanded state.

For some applications, a length of the self-curving longitudinal portion of the stent-graft, measured along the central longitudinal axis of the self-curving longitudinal portion of the stent-graft, is between 4 and 10 cm, when the stent-graft is unconstrained in the radially-expanded state.

For some applications, the one or more blood-impervious flexible sheets include polyethylene terephthalate. For some applications, the one or more blood-impervious flexible sheets include expanded PTFE. For some applications, the circumferential strut members, the compression-generation spring, and the anti-buckling spring include a flexible metal. For some applications, the metal includes a super-elastic alloy. For some applications, the alloy includes Nitinol.

For some applications, transvascularly introducing includes transvascularly introducing the stent-graft while the stent-graft is removably disposed in an elongate delivery tube in the radially-compressed delivery state, and a ratio of (a) an average circumference of the stent-graft when in the radially-expanded state to (b) an inner circumference of the elongate delivery tube is at least 7.

For some applications, an angle about the central longitudinal axis of the self-curving longitudinal portion of the stent-graft between the anti-buckling spring and the compression-generation spring, averaged along the self-curving longitudinal portion of the stent-graft, is between 140 and 220 degrees, e.g., between 160 and 200 degrees, when the stent-graft is unconstrained in the radially-expanded state.

For some applications, the stent-graft includes a plurality of anti-buckling springs.

For some applications, respective average circumferential angles about the central longitudinal axis of the self-curving longitudinal portion of the stent-graft between the anti-buckling springs and the compression-generation spring, averaged along the self-curving longitudinal portion of the stent-graft, are between 140 and 220 degrees, e.g., between 160 and 200 degrees, when the stent-graft is unconstrained in the radially-expanded state.

For some applications, when the stent-graft is unconstrained in the radially-expanded state:
  the anti-buckling springs are disposed at an average circumferential location about the central longitudinal axis of the self-curving longitudinal portion of the stent-graft, and
  an angle about the central longitudinal axis of the self-curving longitudinal portion of the stent-graft between the average circumferential location and the compression-generation spring, averaged along the self-curving longitudinal portion of the stent-graft, is between 140 and 220 degrees, such as between 160 and 200 degrees.

For some applications, a collective longitudinal spring constant of the anti-buckling springs in combination is 70 N/m to 300 N/m.

For some applications, the stent-graft includes a plurality of compression-generation springs.

For some applications, respective average circumferential angles about the central longitudinal axis of the self-curving longitudinal portion of the stent-graft between the anti-buckling spring and the compression-generation springs, averaged along the self-curving longitudinal portion of the stent-graft, are between 140 and 220 degrees, when the stent-graft is unconstrained in the radially-expanded state.

For some applications, the respective average circumferential angles are between 160 and 200 degrees.

For some applications, when the stent-graft is unconstrained in the radially-expanded state:
  the compression-generation springs are disposed at an average circumferential location about the central longitudinal axis of the self-curving longitudinal portion of the stent-graft, and an angle about the central longitudinal axis of the self-curving longitudinal portion of the stent-graft between the average circumferential location and the anti-buckling spring, averaged along the self-curving longitudinal portion of the stent-graft, is between 140 and 220 degrees, such as between 160 and 200 degrees.

For some applications, a collective longitudinal spring constant of the compression-generation springs in combination is 70 N/m to 300 N/m.

There is further provided, in accordance with an application of the present invention, a method for treating a subject, including:

transvascularly introducing a generally tubular endovascular self-curving stent-graft into a blood vessel of the subject while the stent-graft is in a radially-compressed delivery state, which stent-graft (1) includes a self-curving longitudinal portion having proximal and distal ends, (2) is configured to transition from the radially-compressed delivery state to a radially-expanded state, wherein, when the stent-graft is unconstrained in the radially-expanded state, the self-curving longitudinal portion of the stent-graft is curved so as to define an innermost curve and an outermost curve, and (3) includes:
  (i) a plurality of circumferential strut members, disposed at respective axial positions along the self-curving longitudinal portion of the stent-graft, surrounding a central longitudinal axis of the self-curving longitudinal portion of the stent-graft;
  (ii) a graft member, which includes one or more substantially blood-impervious flexible sheets, and which is fixed to the circumferential strut members;
  (iii) a compression-generation spring, which (a) is in an elongated configuration when the stent-graft is in the radially-compressed state, and (b) overlaps respective first portions of at least two of the circumferential strut members; and
  (iv) an anti-buckling spring, which overlaps respective second portions of at least two of the circumferential strut members,
  wherein the anti-buckling spring and the compression-generation spring are together configured to curve the self-curving longitudinal portion of the stent-graft when the stent-graft is unconstrained in the radially-expanded state, such that (A) a lesser length of the self-curving longitudinal portion of the stent-graft, measured along the innermost curve, is less than 75% of a greater length of the self-curving longitudinal portion of the stent-graft, measured along the outermost curve, and (B) a tilt angle between (a) a central longitudinal axis of a proximal-most one of the circumferential strut members and (b) a central longitudinal axis of a distal-most one of the circumferential strut members is at least 20 degrees; and
creating a tight seal between the graft member at the proximal end of the self-curving longitudinal portion of the stent-graft and a wall of the curved blood vessel, by transitioning the stent-graft to the radially-expanded state in the curved blood vessel.

For some applications, the tilt angle is at least 30 degrees, such as at least 45 degrees, when the stent-graft is unconstrained in the radially-expanded state.

For some applications, the stent-graft further includes a distal straight portion, when the stent-graft is unconstrained in the radially-expanded state.

For some applications, an angle between (a) the central longitudinal axis of the proximal-most one of the circumferential strut members and (b) a straight central longitudinal axis of the distal straight portion is at least 20 degrees, when the stent-graft is unconstrained in the radially-expanded state.

The present invention will be more fully understood from the following detailed description of embodiments thereof, taken together with the drawings, in which:

BRIEF DESCRIPTION OF THE DRAWINGS

FIGS. 3A-C are additional schematic illustrations of the stent-graft of FIGS. 2A-B, in accordance with an application of the present invention;

DETAILED DESCRIPTION OF APPLICATIONS

Figure 1:
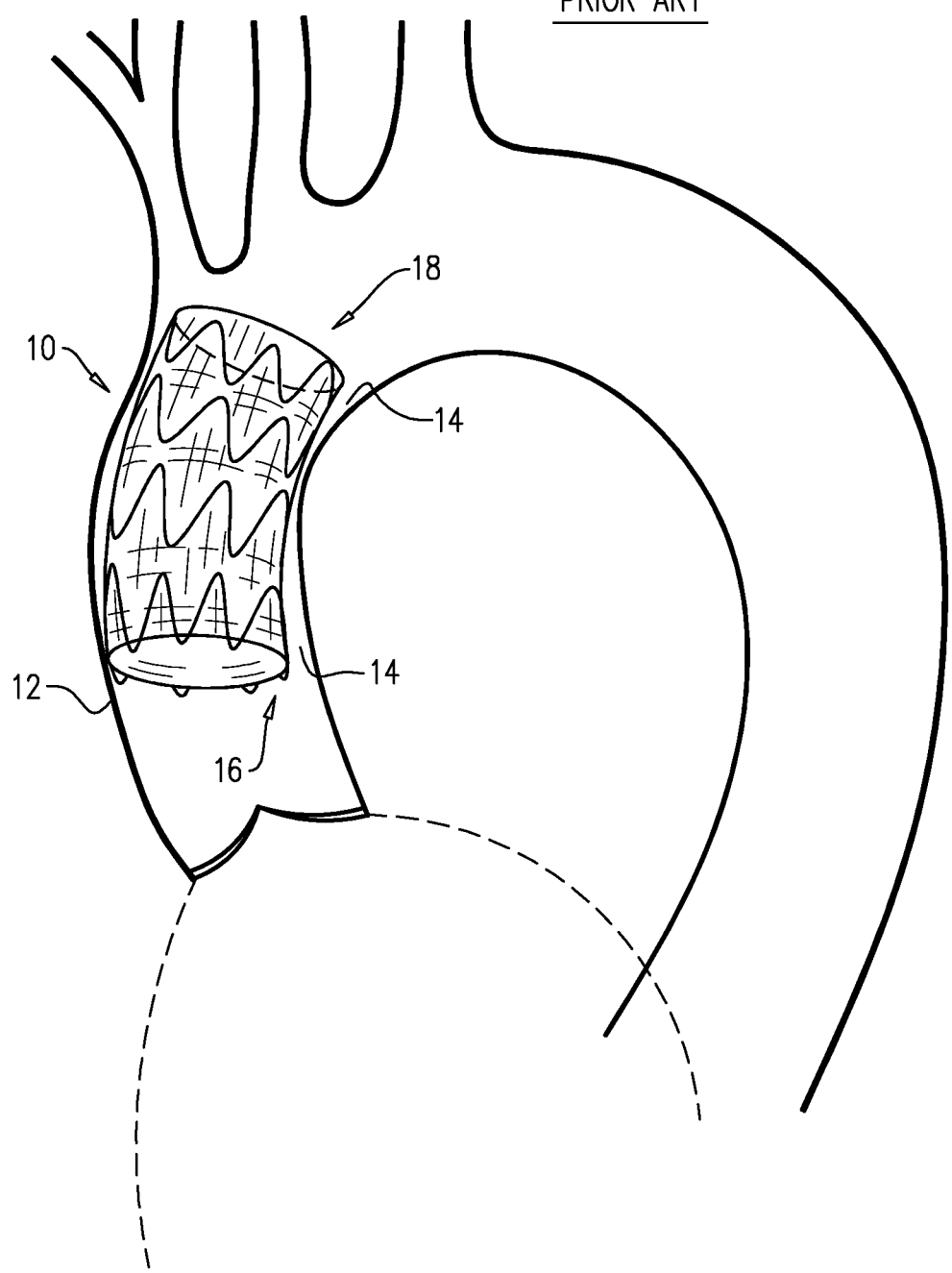
FIG. 1 is a schematic illustration of a stent-graft deployed in the ascending aorta, as known in the prior art.
Figure 2A:
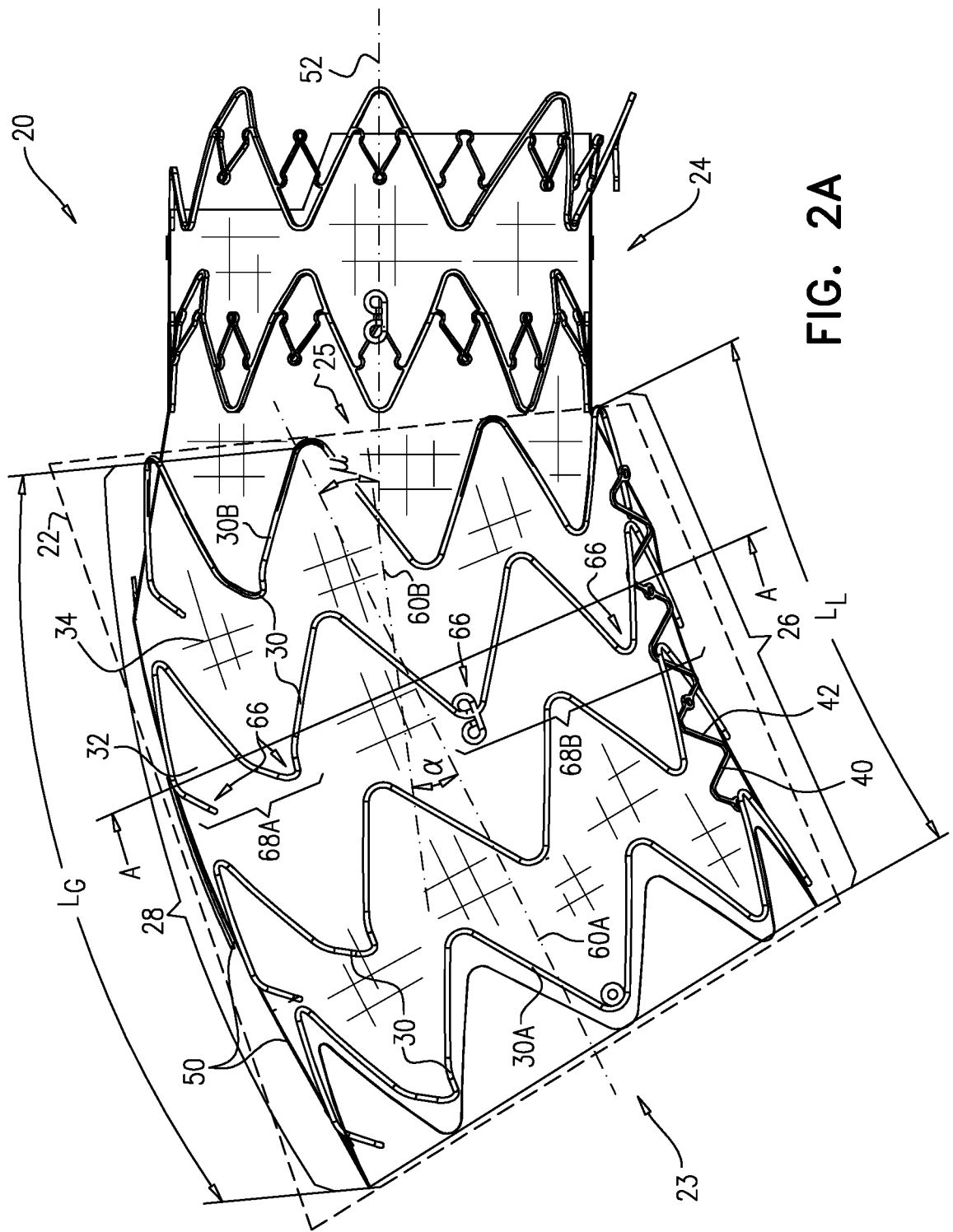
FIGS. 2A-B are schematic illustrations of a generally tubular endovascular stent-graft, in accordance with an application of the present invention.
Figure 2B:
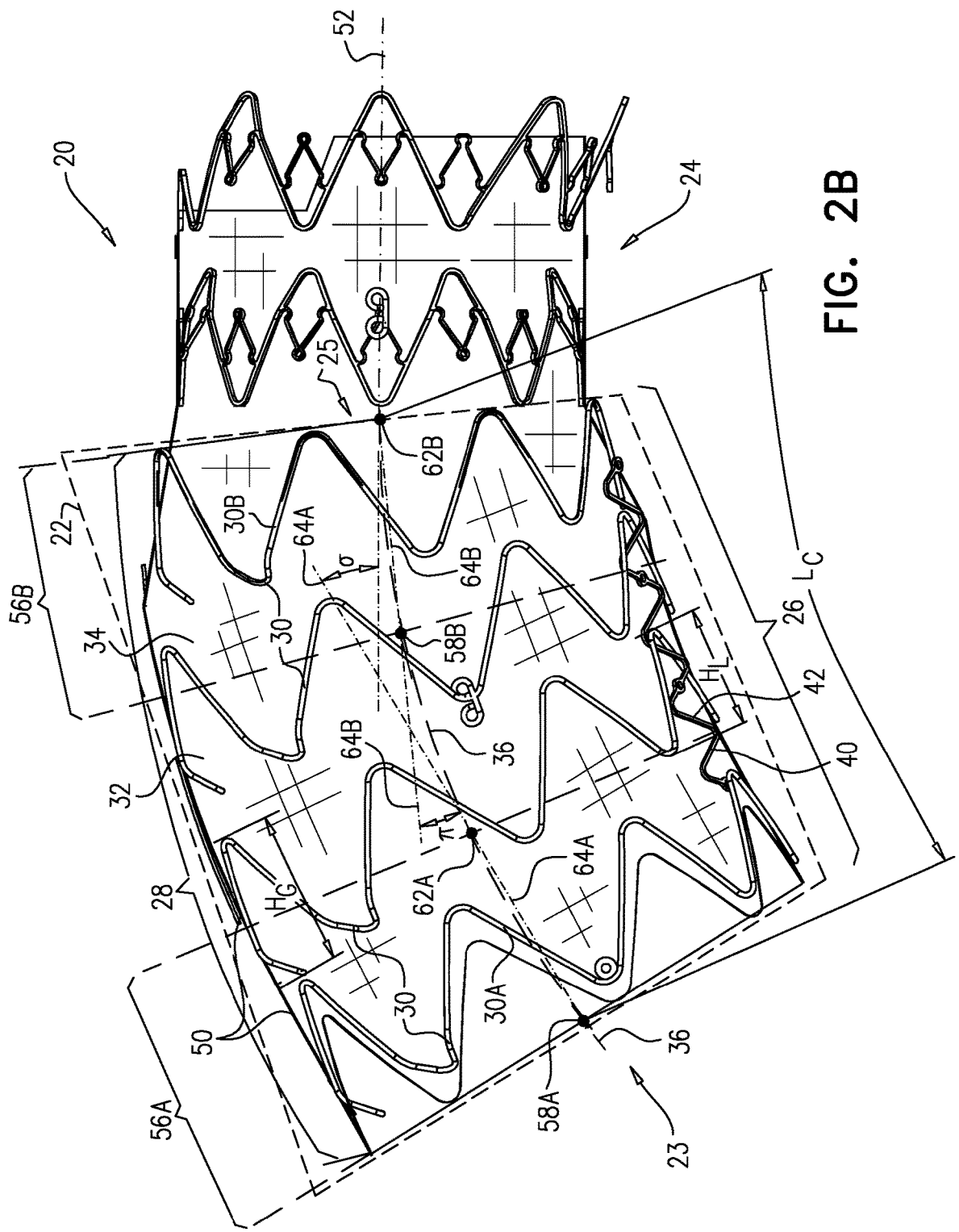

FIGS. 2A-B are schematic illustrations of a generally tubular endovascular stent-graft 20, in accordance with an application of the present invention. FIGS. 2A-B show stent-graft 20 unconstrained in a radially-expanded state, i.e., when no constraining forces are applied to the stent-graft by a deployment tool (such as a delivery catheter) or anatomy of the subject (such as the walls of a blood vessel).

FIGS. 3A-C are additional schematic illustrations of stent-graft 20, in accordance with an application of the present invention. FIGS. 3A-C show stent-graft 20 in the radially-expanded state if stent-graft 20 were to be placed in a right circular cylinder 21 while in the radially-expanded state, such that the right circular cylinder constrains a self-curving longitudinal portion 22 of the stent-graft into a straight configuration. It is to be understood that right circular cylinder 21 is not an element of the invention, but is rather used to describe structural properties of stent-graft 20; during actual deployment and use of stent-graft 20, right circular cylinder 21 is not used.

Stent-graft 20 comprises self-curving longitudinal portion 22; optionally, one or more straight portions 24 (exactly one distal straight portion 24 is shown in the figures); and, optionally, one or more additional curved portions (not shown in the figures). Self-curving longitudinal portion 22 has proximal and distal ends 23 and 25. For some applications, self-curving longitudinal portion 22 of stent-graft 20 longitudinally extends along less than 100% (e.g., less than 80%) of stent-graft 20 (as shown in FIGS. 2A-B), while for other applications, self-curving longitudinal portion 22 of stent-graft 20 longitudinally extends along 100% of stent-graft 20, i.e., no straight portions 24 are provided (configuration not shown). For some applications, an average circumference self-curving longitudinal portion 22 of stent-graft 20 is between 9 and 16 cm, when stent-graft 20 is unconstrained in the radially-expanded state.

Stent-graft 20 is configured to transition from a radially-compressed delivery state (not shown in FIGS. 2A-B or FIGS. 3A-C) to the radially-expanded state (as shown in FIGS. 2A-B and 3A-C). Typically, stent-graft 20 is constrained in the radially-compressed delivery state and relaxed in the radially-expanded state, such that the stent-graft 20 automatically transitions to the radially-expanded state when released from being constrained (such as in a delivery tube, as described hereinbelow with reference to FIGS. 5 and 6). In other words, stent-graft 20 is typically self-expanding. When the stent-graft, which is properly oversized relative to the target blood vessel, is allowed to transition to the self-expanded state in such blood vessel, the wall of the blood vessel constrains the stent-graft from expanding as much as when the stent-graft is unconstrained in the radially-expanded state. Typically, upon release from the delivery tube, compression-generation spring 40 effects a shortening of the stent-graft, along its corresponding nominal circumferential angle, whereas anti-buckling spring 50 resists such longitudinal compression of the stent-graft along its respective circumferential angle.

Stent-graft 20 comprises a plurality of circumferential strut members 30, disposed at respective axial positions along self-curving longitudinal portion 22 of stent-graft 20, surrounding a central longitudinal axis 36 of self-curving longitudinal portion 22 of stent-graft 20 (labeled in FIG. 2B). For some applications, circumferential strut members 30 are serpentine (as shown), sinusoidal (configuration not shown), diamond-shaped (configuration not shown), or other stent shapes known in the art.

Stent-graft 20 also comprises a graft member 32, which is fixed to circumferential strut members 30. For some applications, a centerline length $L_C$ of self-curving longitudinal portion 22 of stent-graft 20 (labeled in FIG. 2B), measured along central longitudinal axis 36 of self-curving longitudinal portion 22 of stent-graft 20, is between 4 and 10 cm, when stent-graft 20 is unconstrained in the radially-expanded state.

As used in the present application, including in the claims, a "central longitudinal axis" of an elongate structure is the set of all centroids of transverse cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.) The central longitudinal axis of a curved elongate structure is curved, rather than straight.

Self-curving longitudinal portion 22 comprises both a plurality of the circumferential strut members 30 and at least a portion of the graft member 32.

When stent-graft 20 is unconstrained in the radially-expanded state, as shown in FIGS. 2A-B, self-curving longitudinal portion 22 of stent-graft 20 is curved so as to define an innermost curve 26 and an outermost curve 28. As used in the present application, including in the claims, the "innermost curve" is the shortest curve along a wall of self-curving longitudinal portion 22 between the axial ends of self-curving longitudinal portion 22 at a constant circumferential location about central longitudinal axis 36 (i.e., a constant "o'clock"). As used in the present application, including in the claims, the "outermost curve" is the longest curve along the wall of self-curving longitudinal portion 22 between the axial ends of self-curving longitudinal portion 22 at a constant circumferential location about central longitudinal axis 36 (i.e., a constant "o'clock").

Graft member 32 comprises one or more biologically-compatible substantially blood-impervious flexible sheets 34, and is attached (such as by stitching) to at least a portion of circumferential strut members 30, on either side (or a portion inside and a portion outside) of the surfaces defined by circumferential strut members 30, so as to define a lumens through stent-graft 20. For example, the circumferential strut members 30 of self-curving longitudinal portion 22 may be fixed inside of graft member 32, and the circumferential strut members 30 of the one or more straight portions 24 may be fixed outside of graft member 32. The flexible sheets may comprise, for example, a polymeric material (e.g., a polyester, or polytetrafluoroethylene), a textile material (e.g., polyethylene terephthalate (PET), or expanded polytetrafluoroethylene (ePTFE)), natural tissue (e.g., saphenous vein or collagen), or a combination thereof.

Stent-graft 20 further comprises a compression-generation spring 40, which is in an elongated configuration (i.e., it is longer than when in its relaxed state), when stent-graft 20 is in the radially-compressed state. Compression-generation spring 40 is configured to apply a longitudinally compressive force to the stent-graft. For some applications, stent-graft 20 comprises a plurality of compression-generation springs 40, such as shown in FIGS. 3A-C and 4D-F.

Compression-generation spring 40 overlaps respective first portions 44 of at least two of circumferential strut members 30, such as at least three of circumferential strut members 30, or at least four of circumferential strut members 30 (as shown in the figures). For some applications, compression-generation spring 40 is fixed to graft member 32 at a plurality of locations on the graft member. Alternatively or additionally, compression-generation spring 40 is fixed to the respective first portions of the at least two of circumferential strut members 30, thereby indirectly fixing compression-generation spring 40 to graft member 32 via the at least two of circumferential strut members 30. Compression-generation spring 40 typically longitudinally extends along at least 60% (typically along at least 80%, such as along 100%) of self-curving longitudinal portion 22.

Stent-graft 20 additionally comprises an anti-buckling spring 50. Anti-buckling spring 50 is configured to resist longitudinal compression of the stent-graft along its respective circumferential angle. Anti-buckling spring 50 overlaps respective second portions 54 of at least two of circumferential strut members 30, such as at least three of circumferential strut members 30, or at least four of circumferential strut members 30 (as shown in the figures). The at least two circumferential strut members 30 are optionally, but not necessarily, the same as the at least two circumferential strut members 30 overlapped by compression-generation spring 40. For some applications, anti-buckling spring 50 is fixed to graft member 32 at a plurality of locations on the graft member. Alternatively or additionally, anti-buckling spring 50 is fixed to the respective second portions of the at least two of circumferential strut members 30, thereby indirectly fixing anti-buckling spring 50 to the graft member via the at least two of circumferential strut members 30. For some applications, stent-graft 20 comprises a plurality of anti-buckling springs 50, such as shown in FIGS. 4B and 4F. Anti-buckling spring 50 typically longitudinally extends along at least 60% (typically along at least 80%, such as 100%) of self-curving longitudinal portion 22.

In some configurations, anti-buckling spring 50 is in a substantially relaxed configuration when stent-graft 20 is unconstrained in the radially-expanded state. In other configurations, anti-buckling spring 50 is in a longitudinally-compressed configuration when stent-graft 20 is unconstrained in the radially-expanded state. In both of these configurations, anti-buckling spring 50 is biased to resist axial compression, and is typically biased to lengthen when stent-graft 20 is in the radially-expanded state and is longitudinally expanded to the maximum length allowed by graft member 32, but is prevented from lengthening by graft member 32. As mentioned above, anti-buckling spring 50 is directly or indirectly fixed to graft member 32 at a plurality of locations on the graft member, at least near its proximal and distal ends, which prevents the graft member from longitudinally over-collapsing, and prevents anti-buckling spring 50 from lengthening the outermost curve 28 of self-curving longitudinal portion 22.

For some applications, anti-buckling spring 50 is shaped so as to define a plurality of curves (e.g., is sinusoidal or serpentine), and is in fixed orientation with respect to graft member 32 such that the curves reside substantially in a plane that is substantially parallel to the surface of graft member 32. As a result, if anti-buckling spring 50 is axially deformed during or after deployment, the anti-buckling spring does not press against the wall of the blood vessel or create large inward crests in the graft member, as it might do if the planes of the curves were perpendicular to the surface of the graft member. In addition, the curves define predetermined strain-distribution locations; without such strain-distribution locations, the anti-buckling spring, if axially deformed, might undergo plastic deformation and/or snap.

Anti-buckling spring 50 and compression-generation spring 40 are together configured to curve self-curving longitudinal portion of stent-graft 20 when stent-graft 20 is unconstrained in the radially-expanded state, as shown in FIGS. 2A-B, such that a lesser length $L_L$ of self-curving longitudinal portion 22 of stent-graft 20, measured along innermost curve 26, is less than 85%, such as less than 80%, such as less than 75% or less than 70%, of a greater length $L_G$ of self-curving longitudinal portion 22 of stent-graft 20, measured along outermost curve 28.

For some applications, when stent-graft 20 is unconstrained in the radially-expanded state, as shown in FIGS. 2A-B, stent-graft 20 is characterized by one or both of the following:
 (i) a proximal-most third 56A of self-curving longitudinal portion 22, measured along central longitudinal axis 36 of self-curving longitudinal portion 22, has proximal-most and distal-most center points 58A and 62A on central longitudinal axis 36, which points together define a proximal-third straight line 64A, (ii) a distal-most third 56B of self-curving longitudinal portion 22, measured along central longitudinal axis 36 of self-curving longitudinal portion 22, has proximal-most and distal-most center points 58B and 62B on central longitudinal axis 36, which points together define a distal-third straight line 64B, and (iii) a first tilt angle π (pi) between (a) proximal-third straight line 64A and (b) distal-third straight line 64B is at least 15 degrees, such as at least 20 degrees, at least 25 degrees, at least 30 degrees, or at least 45 degrees, as labeled in FIG. 2B (it is noted that a length of proximal-most third 56A, measured along central longitudinal axis 36 of self-curving longitudinal portion 22, equals one-third of centerline length $L_C$ of self-curving longitudinal portion 22, and a length of distal-most third 56B, measured along central longitudinal axis 36 of self-curving longitudinal portion 22, equals one-third of centerline length $L_C$ of self-curving longitudinal portion 22); and/or a second tilt angle α (alpha) between (a) a central longitudinal axis 60A of a proximal-most one 30A of circumferential strut members 30 and (b) a central longitudinal axis 60B of a distal-most one 30B of circumferential strut members 30 is at least 15 degrees, such as at least 20 degrees, at least 25 degrees, at least 30 degrees, or at least 45 degrees, as labeled in FIG. 2A.

(As used in the present application, including in the claims, an angle between two lines is the smaller of the two supplementary angles between the two lines, or equals 90 degrees if the two lines are perpendicular.)

For some applications, a longitudinal spring constant of compression-generation spring 40 is at least 70 N/m, no more than 300 N/m, and/or 70 N/m to 300 N/m. For some applications in which stent-graft 20 comprises a plurality of compression-generation springs 40, such as shown in FIGS. 3A-C and 4D-F, a collective longitudinal spring constant of compression-generation springs 40 in combination is at least 70 N/m, no more than 300 N/m, and/or 70 N/m to 300 N/m. Alternatively or additionally, for some applications, a longitudinal spring constant of anti-buckling spring 50 is at least 70 N/m, no more than 300 N/m, and/or 70 N/m to 300 N/m. For some applications in which stent-graft 20 comprises a plurality of anti-buckling springs 50, such as shown in FIGS. 4B and 4F, a collective longitudinal spring constant of anti-buckling spring 50 in combination is at least 70 N/m, no more than 300 N/m, and/or 70 N/m to 300 N/m. For some applications, if stent-graft 20 were to be placed in right circular cylinder 21 while in the radially-expanded state, as shown in FIGS. 3A-C, an axial compression force exerted by compression-generation spring 40 against an inner surface of the cylinder would be 3 to 10 N.

As labeled in FIG. 2B, for some applications in which stent-graft 20 comprises distal straight portion 24, an angle σ (sigma) between (a) proximal-third straight line 64A and (b) a straight central longitudinal axis 52 of the distal straight portion is at least 20 degrees, such as at least 25 degrees, when stent-graft 20 is unconstrained in the radially-expanded state. Alternatively or additionally, as labeled in FIG. 2A, for some applications in which stent-graft 20 comprises distal straight portion 24, an angle μ (mu) between (a) central longitudinal axis 60A of the proximal-most circumferential strut member 30A and (b) straight central longitudinal axis 52 of the distal straight portion is at least 20 degrees, when stent-graft 20 is unconstrained in the radially-expanded state.

For some applications, when stent-graft 20 is in unconstrained in the radially-expanded state, as shown in FIGS. 2A-B:
 the lesser length $L_L$ of self-curving longitudinal portion 22 of stent-graft 20, measured along innermost curve 26 of self-curving longitudinal portion 22 of stent-graft 20, is at least 15% less than a centerline length $L_C$ of self-curving longitudinal portion 22 of stent-graft 20, measured along central longitudinal axis 36 of self-curving longitudinal portion 22 of stent-graft 20; and/or
 the greater length $L_G$ of self-curving longitudinal portion 22 of stent-graft 20, measured along outermost curve 28 of self-curving longitudinal portion 22 of stent-graft 20, is at least 15% greater than a centerline length $L_C$ of self-curving longitudinal portion 22 of stent-graft 20, measured along central longitudinal axis 36 of self-curving longitudinal portion 22 of stent-graft 20.

For some applications, a length of compression-generation spring 40 is at least 15% greater, such as at least 20% greater, when stent-graft 20 is in the radially-compressed delivery state than when stent-graft 20 is unconstrained in the radially-expanded state. Alternatively or additionally, for some applications, a length of compression-generation spring 40 is at least 10%, such as least 15% or 20% less, when stent-graft 20 is unconstrained in the radially-expanded state than when stent-graft 20 is in the radially-compressed delivery state.

For some applications, a length of anti-buckling spring 50 is no more than 10% greater (e.g., no more than 5% greater, or no greater) when stent-graft 20 is in the radially-compressed delivery state than when stent-graft 20 is unconstrained in the radially-expanded state. Alternatively or additionally, for some applications, a length of anti-buckling spring 50 is no less (e.g., is greater) when stent-graft 20 is unconstrained in the radially-expanded state than when stent-graft 20 is in the radially-compressed delivery state.

For some applications, anti-buckling spring 50 comprises exactly one structural strut element, such as shown in the figures. For these applications, an average circumferential location of anti-buckling spring 50 typically coincides with outermost curve 28 (i.e., a greater curve) of self-curving longitudinal portion 22. Alternatively or additionally, for some applications, compression-generation spring 40 comprises exactly one structural strut element, such as shown in the figures. For these applications, an average circumferential location of compression-generation spring 40 typically coincides with innermost curve 26 (i.e., a lesser curve) of self-curving longitudinal portion 22.

Typically, circumferential strut members 30, compression-generation spring 40, and/or anti-buckling spring 50 comprise a metal, such as a flexible metal, an elastic metal, stainless steel, or a superelastic alloy (such as Nitinol).

For some applications, a height $H_G$ at outermost curve 28 of each of circumferential strut members 30 of self-curving longitudinal portion 22 of stent-graft 20, is greater than (e.g., at least 120% of) a height $H_G$ at innermost curve 26, both $H_G$ and $H_L$ measured along stent-graft 20, when stent-graft 20 is unconstrained in the radially-expanded state.

Reference is again made to FIGS. 2A-B. For some applications, an average radius of curvature of outermost curve 28 equals at least 120%, e.g., at least 130% or at least 140%, of an average radius of curvature of innermost curve 26, with both average radii of curvature measured along self-curving longitudinal portion 22 when stent-graft 20 is unconstrained in the radially-expanded state. Alternatively or additionally, for some applications, the average radius of curvature of innermost curve 26 is at least 4 cm, no more than 8 cm, and/or between 4 and 8 cm, measured along self-curving longitudinal portion 22 when stent-graft 21) is unconstrained in the radially-expanded state.

Reference is now made to FIGS. 2A and 3A-C. For some applications, each of circumferential strut members 30 of self-curving longitudinal portion 22 is shaped so as to define a plurality of proximal peaks 66, e.g., 6 to 20 proximal peaks 66, such as 8 proximal peaks 66. For some applications, when stent-graft 20 is unconstrained in the radially-expanded state, for at least one of circumferential strut members 30 of self-curving longitudinal portion 22:

a first set 68A of proximal peaks 66 of the circumferential strut member 30, which includes at least a circumferentially-closest one of proximal peaks 66 to outermost curve 28 of self-curving longitudinal portion 22, and no more than half of proximal peaks 66 of the circumferential strut member 30, are bent radially inward at least an average angle of 20 degrees toward central longitudinal axis 36 of self-curving longitudinal portion 22, and a second set 68B of proximal peaks 66 of the circumferential strut member 30, which includes all of proximal peaks 66 of the circumferential strut member 30 not in first set 66A, are not bent radially inward by an average angle of at least 20 degrees toward central longitudinal axis 36 of self-curving longitudinal portion 22.

Such inward bending of at least a portion of proximal peaks 66 on the outer side of self-curving longitudinal portion 22 avoid possible puncturing of the graft member, and/or the wall of the blood vessel by the proximal peaks.

For some applications, first set 68A includes no more than 40% of proximal peaks 66 of the circumferential strut member 30 (e.g., three of the eight proximal peaks 66 of each of circumferential strut member 30, as shown in FIGS. 2A and 3A-B). For some applications, first set 68A includes exactly one of proximal peaks 66 of the circumferential strut member 30.

For some application, one or more of the distal peaks of one or more of circumferential strut members 30 of self-curving longitudinal portion 22 are also be bent radially inward.

Reference is now made to FIGS. 4A-F, which are schematic cross-sectional views of stent-graft 20 unconstrained in the radially-expanded state, taken along line A-A of FIG. 2A, in accordance with respective applications of the present invention.

Figure 4A:
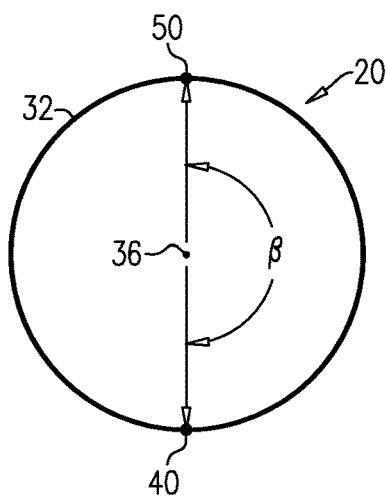
FIGS. 4A-F are schematic cross-sectional views of the stent-graft of FIGS. 2A-B and 3A-C unconstrained in the radially-expanded state, taken along line A-A of FIG. 2A, in accordance with respective applications of the present invention.
Figure 4B:
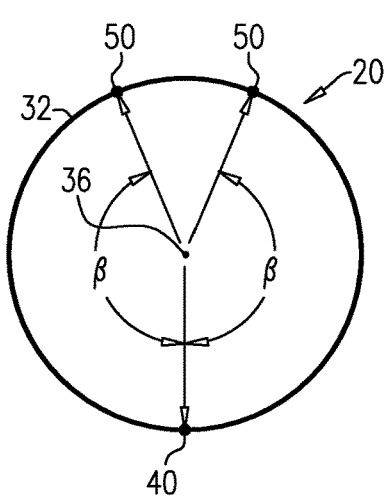

For some applications, such as shown in FIG. 4A, an angle β (beta) about central longitudinal axis 36 of self-curving longitudinal portion 22 of stent-graft 20 between anti-buckling spring 50 and compression-generation spring 40, averaged along self-curving longitudinal portion 22 of stent-graft 20, is between 140 and 220 degrees, such as between 160 and 200 degrees (e.g., 180 degrees, as shown), when stent-graft 20 is unconstrained in the radially-expanded state. For applications in which anti-buckling spring 50 and compression-generation spring 40 are at respective constant circumferential positions along self-curving longitudinal portion 22 of stent-graft 20, the averaged angle β (beta) equals the constant angle between the springs. For applications in which the circumferential position of one or both of anti-buckling spring 50 and compression-generation spring 40 varies along self-curving longitudinal portion 22 of stent-graft 20, the angle β (beta) equals the angle between the springs averaged along the self-curving longitudinal portion. In the configuration shown in FIG. 4A, stent-graft 20 is shown comprising exactly one anti-buckling spring 50 and exactly one compression-generation spring 40.

For some applications in which stent-graft 20 comprises a plurality of anti-buckling springs 50, such as shown in FIG. 4B, respective average circumferential angles β (beta) about central longitudinal axis 36 of self-curving longitudinal portion 22 of stent-graft 20 between anti-buckling springs 50 and compression-generation spring 40, averaged along self-curving longitudinal portion 22 of stent-graft 20, are between 140 and 220 degrees, such as between 160 and 200 degrees, when stent-graft 20 is unconstrained in the radially-expanded state.

Figure 4C:
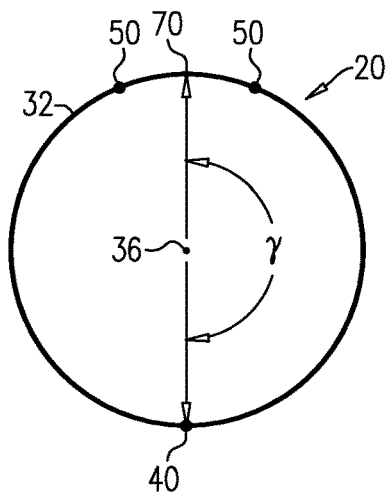

For some applications in which stent-graft 20 comprises a plurality of anti-buckling springs 50, such as shown in FIG. 4C, anti-buckling springs 50 are disposed at an average circumferential location 70 about central longitudinal axis 36 of self-curving longitudinal portion 22 of stent-graft 20, when stent-graft 20 is unconstrained in the radially-expanded state. It is noted that average circumferential location 70 can vary along the stent-graft. An angle γ (gamma) about central longitudinal axis 36 of self-curving longitudinal portion 22 of stent-graft 20 between average circumferential location 70 and compression-generation spring 40, averaged along self-curving longitudinal portion 22 of stent-graft 20, is between 140 and 220 degrees, such as between 160 and 200 degrees (e.g., 180 degrees, as shown), when stent-graft 20 is unconstrained in the radially-expanded state.

For some applications, average circumferential location 70 of anti-buckling springs 50 coincides with outermost curve 28 of self-curving longitudinal portion 22.

Figure 4D:
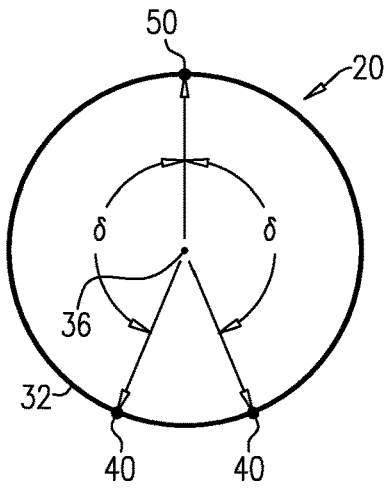

For some applications in which stent-graft 20 comprises a plurality of compression-generation springs 40, such as shown in FIG. 4D, respective average circumferential angles δ (delta) about central longitudinal axis 36 of self-curving longitudinal portion 22 of stent-graft 20 between anti-buckling spring 50 and compression-generation springs 40, averaged along self-curving longitudinal portion 22 of stent-graft 20, are between 140 and 220 degrees, such as between 160 and 200) degrees, when stent-graft 20 is unconstrained in the radially-expanded state.

Figure 4E:
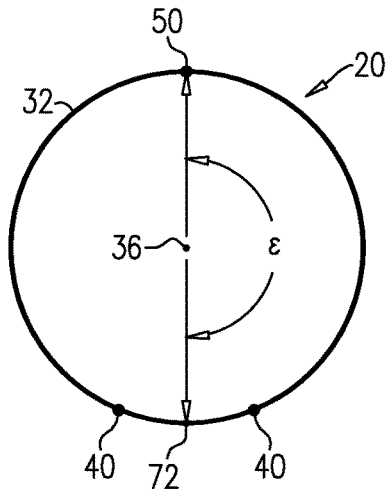
Figure 4F:
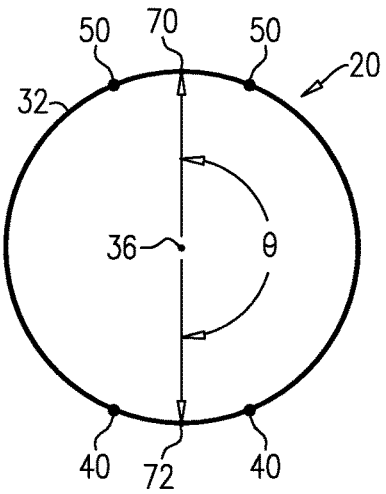

For some applications in which stent-graft 20 comprises a plurality of compression-generation springs 40, such as shown in FIG. 4E, compression-generation springs 40 are disposed at an average circumferential location 72 about central longitudinal axis 36 of self-curving longitudinal portion 22 of stent-graft 20, when stent-graft 20 is unconstrained in the radially-expanded state. It is noted that average circumferential location 72 can vary along the stent-graft. An angle ε (epsilon) about central longitudinal axis 36 of self-curving longitudinal portion 22 of stent-graft 20 between average circumferential location 72 and anti-buckling spring 50, averaged along self-curving longitudinal portion 22 of stent-graft 20, is between 140 and 220 degrees, such as between 160 and 200 degrees, when stent-graft 20 is unconstrained in the radially-expanded state.

For some applications, average circumferential location 72 of compression-generation springs 40 coincides with innermost curve 26 of self-curving longitudinal portion 22.

For some applications in which stent-graft 20 comprises a plurality of anti-buckling springs 50 and a plurality of compression-generation springs 40, such as shown in FIG. 4F, anti-buckling springs 50 are disposed at an average circumferential location 70 about central longitudinal axis 36 of self-curving longitudinal portion 22 of stent-graft 20, and compression-generation springs 40 are disposed at an average circumferential location 72 about central longitudinal axis 36 of self-curving longitudinal portion 22 of stent-graft 20, when stent-graft 20 is unconstrained in the radially-expanded state. It is noted that average circumferential locations 70 and 72 can vary along the stent-graft. An angle θ (theta) about central longitudinal axis 36 of self-curving longitudinal portion 22 of stent-graft 20 between average circumferential location 70 and average circumferential location 72, averaged along self-curving longitudinal portion 22 of stent-graft 20, is between 140 and 220 degrees, such as between 160 and 200 degrees (e.g., 180 degrees, as shown), when stent-graft 20 is unconstrained in the radially-expanded state.

Reference is again made to FIGS. 3A-C. For some applications, if stent-graft 20 were to be (a) placed in right circular cylinder 21 while in the radially-expanded state, such that the right circular cylinder constrains self-curving longitudinal portion 22 of stent-graft 20 into a straight configuration:

each of the one or more compression-generation springs 40 of stent-graft 20 would be substantially longitudinally-disposed, and/or each of the one or more anti-buckling springs 50 of stent-graft 20 would be substantially longitudinally-disposed.

As used in the present application, including in the claims, "substantially longitudinally-disposed" means, for each of the springs, that:

if stent-graft 20 were to be (a) placed in right circular cylinder 21 while in the radially-expanded state, such that the right circular cylinder constrains self-curving longitudinal portion 22 of stent-graft 20 into a straight configuration, (b) cut along a cut line parallel to a straightened central longitudinal axis of straightened self-curving longitudinal portion 22, and then (c) unrolled into a flat state, while maintaining the respective constrained lengths of compression-generation spring(s) 40 and anti-buckling spring(s) 50, then the cut line would form an angle of no more than 30 degrees with a line between the two endpoints of the spring.

Typically, when stent-graft 20 is unconstrained in the radially-expanded, the springs are substantially aligned with central longitudinal axis 36 of self-curving longitudinal portion 22 of stent-graft 20, yet the stents are typically curved, at least when the springs are directly or indirectly fixed to graft member 32 at a plurality of locations on the graft member. If placed in right circular cylinder 21, the springs would still be longitudinal, but now, also linear (i.e., non-curved), since self-curving longitudinal portion 22 of stent-graft 20 would now be straightened.

Figure 5:
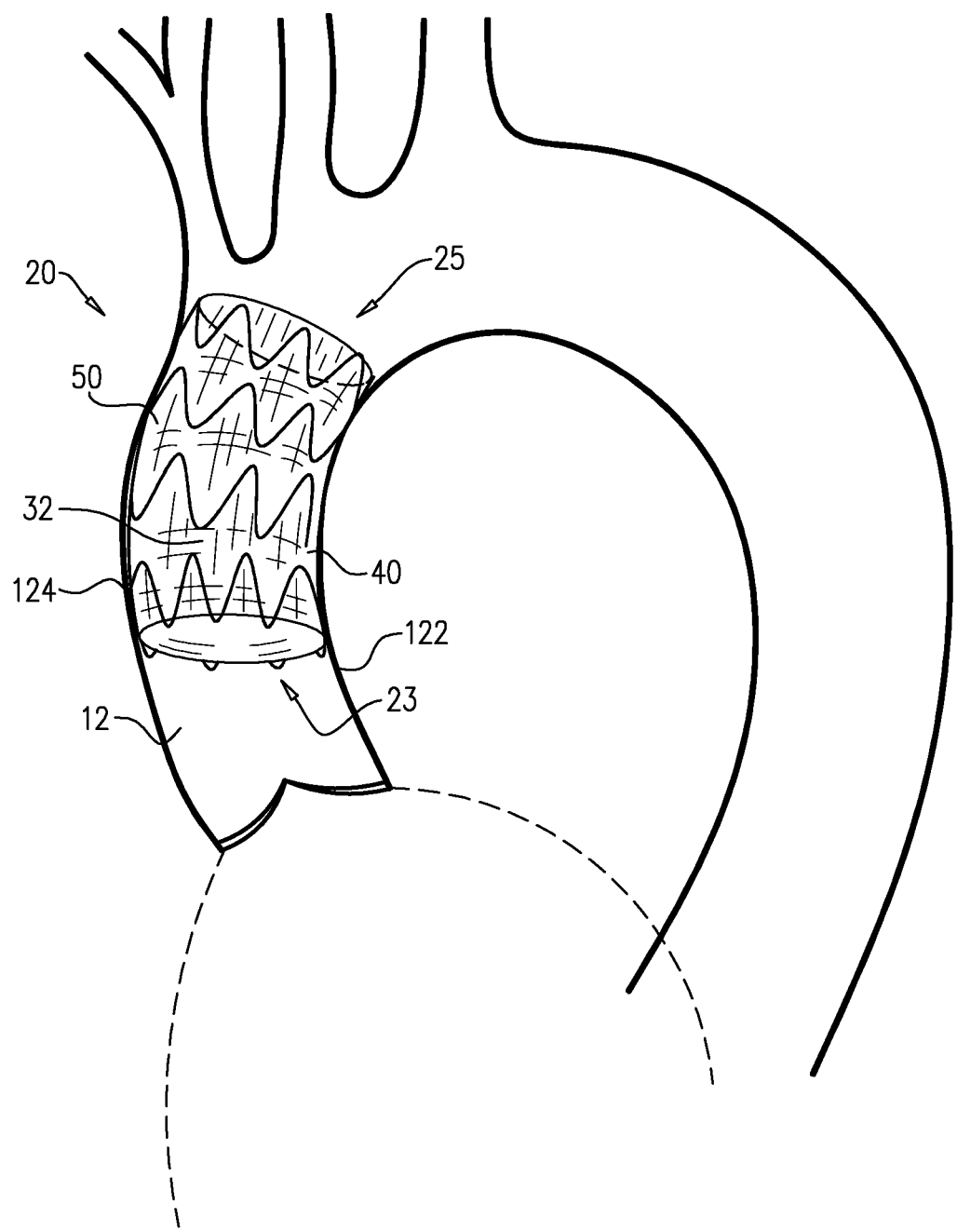
FIGS. 5 and 6 are schematic illustrations of exemplary deployments of the stent-graft of FIGS. 2A-B and 3A-C, in accordance with respective applications of the present invention.
Figure 6:
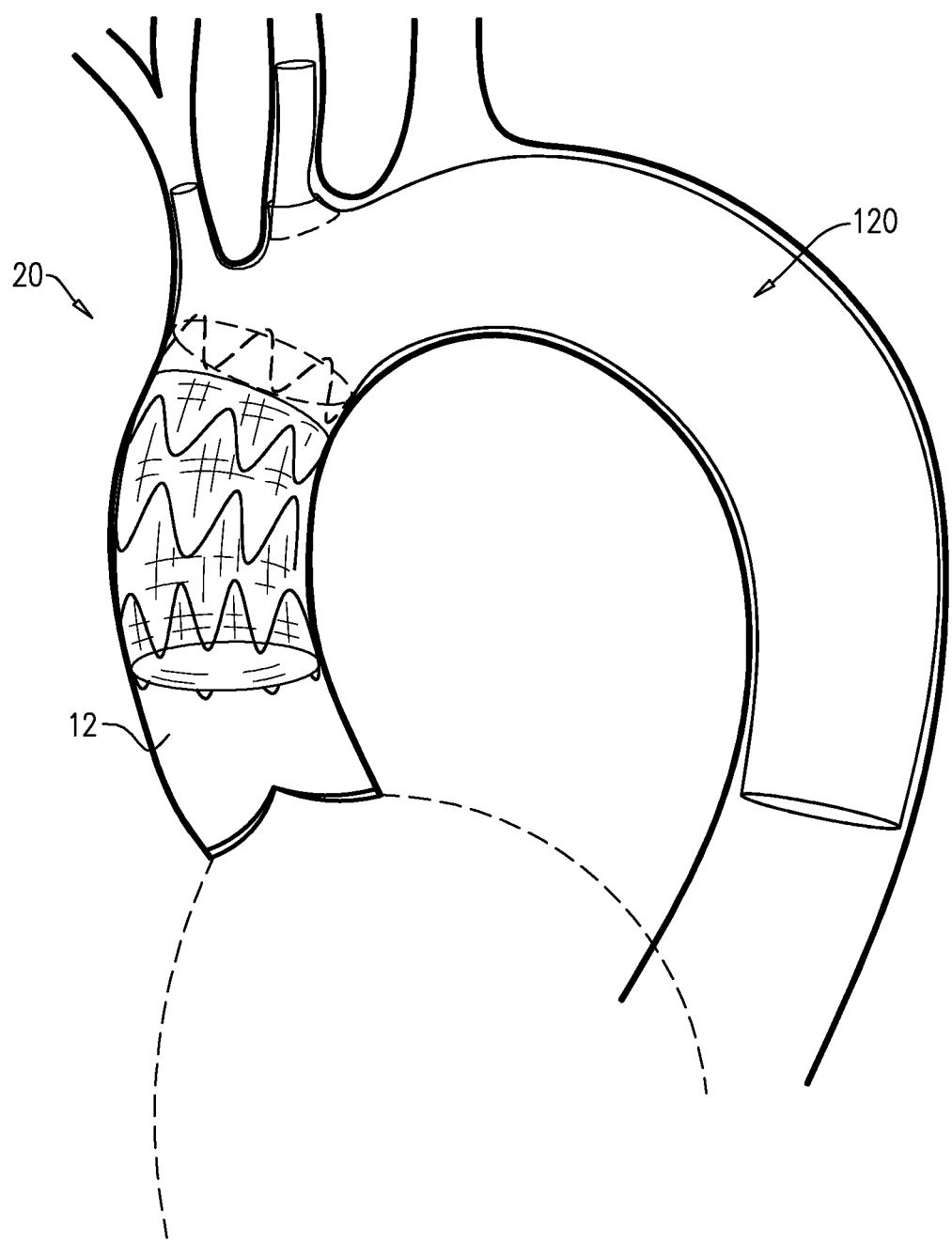

Reference is now made to FIGS. 5 and 6, which are schematic illustrations of exemplary deployments of stent-graft 20, in accordance with respective applications of the present invention. Stent-graft 20 may also be used to treat a blood vessel suffering from a dissection, or, more generally, a pathologically dilated aorta. In the configurations shown in FIGS. 5 and 6, stent-graft 20 is shown deployed in ascending aorta 12, with proximal end 23 upstream of distal end 25, i.e., closer to the heart. Optionally, the techniques described herein are used in combination with the techniques described in US Patent Application Publication 2013/0013050, and/or U.S. Provisional Application 62/093,497, both of which are assigned to the assignee of the present application and incorporated herein by reference.

The deployment is typically performed in a transvascular (typically percutaneous) procedure using one or more guidewires and an elongate delivery tube that is sized to hold stent-graft 20 in the radially-compressed delivery state. For some applications, a ratio of (a) an average circumference of stent-graft 20 when in the radially-expanded state to (b) an inner circumference of the delivery tube is at least 5, such as at least 7. Typically, stent-graft 20 is in its most longitudinally elongated configuration when in the delivery tube.

Typically, after stent-graft 20 is positioned at the desired anatomical site, with at least self-curving longitudinal portion 22 in a curved portion of the blood vessel, the delivery tube is withdrawn proximally, exposing stent-graft 20 and allowing the stent-graft to self-expand into the radially-expanded state. Stent-graft 20 is rotated, typically before deployment from the delivery tube, such that:

compression-generation spring 40 (or average circumferential location 72, if stent-graft 20 comprises a plurality of compression-generation springs 40, as described hereinabove with reference to FIGS. 3A-C and 4D-F) is circumferentially aligned with a lesser curve 122 of ascending aorta 12 (or another blood vessel), and anti-buckling spring 50 (or average circumferential location 70, if stent-graft 20 comprises a plurality of anti-buckling springs 50, as described hereinabove with reference to FIGS. 4B and 4F) is circumferentially aligned with a greater curve 124 of ascending aorta 12 (or the other blood vessel).

The deployment may be performed using deployment techniques known in the an and/or described in any of the patent applications publications and patents incorporated hereinbelow by reference.

The average radius of curvature of innermost curve 26 of self-curving longitudinal portion 22 when stent-graft 20 is unconstrained in the radially-expanded state is typically less than the radius of curvature of lesser curve 122 of the curved blood vessel at the implantation site, thereby creating a tight seal between graft member 32 at both proximal and distal ends 23 and 25 of self-curving longitudinal portion 22 and lesser curve 122 of ascending aorta 12, thereby preventing bird-beaking. In addition, the average radius of curvature of curve outermost curve 28 of self-curving longitudinal portion 22 when stent-graft 20 is unconstrained in the radially-expanded state is typically greater than the radius of curvature of greater curve 124 of the curved blood vessel at the implantation site, thereby creating a tight seal between graft member 32 at both proximal and distal ends 23 and 25 of self-curving longitudinal portion 22 and greater curve 124 of ascending aorta 12, thereby preventing bird-beaking on the outer (longer) side of the self-curving longitudinal portion of the stent-graft.

In addition, the diameter of self-curving longitudinal portion 22 of stent-graft 20 is typically 15-25% greater than the diameter of the site of the curved blood vessel in which the portion is implanted.

Typically, in order to provide good sealing, the curvature and/or diameter of the blood vessel is assessed, and the stent-graft is chosen from a plurality of self-curving stent-grafts having different respective first and/or second tilt angles, different respective diameters, different respective innermost radii of curvature, and/or different respective outermost radii of curvature, or a desired combination of these parameters.

For some applications, such as shown in FIG. 6, one or more additional stent-grafts 120 are sealingly coupled to the proximal or distal ends 23 or 25 of stent-graft 20, and optionally provide blood flow paths to one or more of the branching arteries. (It is noted that in the deployment shown in FIG. 6, blood flow to the left subclavian artery is blocked by stent-graft 120. The left subclavian artery is either "sacrificed" (i.e. via occlusion), or surgically anastomosed to the left common carotid artery, or possibly to another source artery, such as the right common carotid artery. Alternatively, stent-graft 120 may be shaped so as to define an additional lateral fenestration to allow blood flow to the left subclavian artery.)

The scope of the present invention includes embodiments described in the following patents and patent applications, which are assigned to the assignee of the present application and are incorporated herein by reference. In an embodiment, techniques and apparatus described in one or more of the following patent applications are combined with techniques and apparatus described herein. In particular, the stent-grafts described herein may be used as components of the stent-graft systems described in the following patent and patent applications, and deployed as described as described in the following patent and patent applications, mutatis mutandis.

PCT Application PCT/IL2008/000287, filed Mar. 5, 2008, which published as PCT Publication WO 2008/107885

PCT Application PCT/IB2010/052861, filed Jun. 23, 2010, which published as PCT Publication WO 2010/150208

PCT Application PCT/IL2010/000564, filed Jul. 14, 2010, which published as PCT Publication WO 2011/007354

PCT Application PCT/IL2010/000917, filed Nov. 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, filed Dec. 2, 2010, which published as PCT Publication WO 2011/067764

PCT Application PCT/IL2010/001037, filed Dec. 8, 2010, which published as PCT Publication WO 2011/070576

PCT Application PCT/IL2011/000135, filed Feb. 8, 2011, which published as PCT Publication WO 2011/095979

PCT Application PCT/IL2012/000060, filed Feb. 2, 2012, which published as PCT Publication WO 2012/104842

PCT Application PCT/IL2012/000241, filed Jun. 19, 2012, which published as PCT Publication WO 2012/176187

PCT Application PCT/IL2012000300, filed Aug. 12, 2012, which published as PCT Publication WO 2013/030819

U.S. Pat. No. 8,317,856 to Shalev et al.

U.S. Pat. No. 8,574,287 to Benary et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

U.S. application Ser. No. 13/031,871, filed Feb. 22, 2011, which published as US Patent Application Publication 2011/0208289

U.S. Provisional Application 61/496,613, filed Jun. 14, 2011

US Provisional Application 61/499,195, filed Jun. 21, 2011

U.S. Provisional Application 61/505,132, filed Jul. 7, 2011

U.S. Provisional Application 61/529,931, filed Sep. 1, 2011

U.S. Provisional Application 61/553,209, filed Oct. 30, 2011

U.S. application Ser. No. 13/380,278, filed Dec. 22, 2011, which published as US Patent Application Publication 2012/0150274

U.S. application Ser. No. 13/384,075, filed Jan. 13, 2012, which published as US Patent Application Publication 2012/0179236

U.S. application Ser. No. 13/505,996, filed May 3, 2012, which published as US Patent Application Publication 2012/0310324

U.S. application Ser. No. 13/513,397, filed Jun. 1, 2012, which published as US Patent Application Publication 2012/0330399

U.S. application Ser. No. 13/514,240, filed Jun. 6, 2012, which published as US Patent Application Publication 2013/0013051

U.S. Provisional Application 61/678,182, filed Aug. 1, 2012

U.S. application Ser. No. 13/577,161, filed Aug. 3, 2012, which published as US Patent Application Publication 2013/0035751

U.S. application Ser. No. 13/512,778, filed Sep. 24, 2012, which published as US Patent Application Publication 2013/0013050

U.S. application Ser. No. 13/807,880, filed Dec. 31, 2012, which published as US Patent Application Publication 2013/0131783

PCT Application PCT/IL2012/000095, filed Mar. 1, 2012, which published as PCT Publication WO 2012/17395

PCT Application PCT/IL2012/000148, filed Apr. 4, 2012, which published as PCT Publication WO 2013/030818

PCT Application PCT/IL2012/000190, filed May 15, 2012, which published as PCT Publication WO 2013/171730

PCT Application PCT/IL2012/000269, filed Jul. 2, 2012, which published as PCT Publication WO 2013/005207

PCT Application PCT/IL2012/050424, filed Oct. 29, 2012, which published as PCT Publication WO 2013/065040

PCT Application PCT/IL2012/050506, filed Dec. 4, 2012, which published as PCT Publication WO 2013/084235

U.S. Provisional Application 61/749,965, filed Jan. 8, 2013

U.S. application Ser. No. 13/807,906, filed Feb. 8, 2013, which published as US Patent Application Publication 2013/0204343

U.S. Provisional Application 61/775,964, filed Mar. 11, 2013

U.S. Provisional Application 61/826,544, filed May 23, 2013

U.S. application Ser. No. 13/979,551, filed Jul. 12, 2013, which published as US Patent Application Publication 2013/0289587

PCT Application PCT/IL2013/050656, filed Jul. 31, 2013, which published as PCT Publication WO 2014/020609

U.S. Provisional Application 61/906,014, filed Nov. 19, 2013

PCT Application PCT/IL2014/050019, filed Jan. 7, 2014, which published as PCT Publication WO 2014/108895

U.S. Provisional Application 61/926,533, filed Jan. 13, 2014

PCT Application PCT/IL2014/050174, filed Feb. 18, 2014, which published as PCT Publication WO 2014/141232

PCT Application PCT/IL2014/050434, filed May 18, 2014, which published as PCT Publication WO 2014/188412

PCT Application PCT/IL2014/050973, filed Nov. 6, 2014, which published as PCT Publication WO 2015/075708

U.S. Provisional Application 62/093,497, filed Dec. 18, 2014

It will be appreciated by persons skilled in the an that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a generally tubular endovascular self-curving stent-graft, which (a) comprises a self-curving longitudinal portion having proximal and distal ends, (b) is configured to transition from a radially-compressed delivery state to a radially-expanded state, wherein, when the stent-graft is unconstrained in the radially-expanded state, the self-curving longitudinal portion of the stent-graft is curved so as to define an innermost curve and an outermost curve, and (c) comprises:

a plurality of circumferential strut members, disposed at respective axial positions along the self-curving longitudinal portion of the stent-graft, surrounding a central longitudinal axis of the self-curving longitudinal portion of the stent-graft, wherein each of the circumferential strut members of the self-curving longitudinal portion is shaped so as to define a plurality of proximal peaks; and a graft member, which comprises one or more substantially blood-impervious flexible sheets, and which is fixed to the circumferential strut members, wherein, when the stent-graft is unconstrained in the radially-expanded state, for at least one of the circumferential strut members of the self-curving longitudinal portion:

a first set of the proximal peaks of the circumferential strut member, which includes at least a circumferentially-closest one of the proximal peaks to the outermost curve of the self-curving longitudinal portion, and no more than half of the proximal peaks of the circumferential strut member, are bent radially inward at least an average angle of 20 degrees toward the central longitudinal axis of the self-curving longitudinal portion, and a second set of the proximal peaks of the circumferential strut member, which includes all of the proximal peaks of the circumferential strut member not in the first set, are not bent radially inward by at least an average angle of 20 degrees toward the central longitudinal axis of the self-curving longitudinal portion.

2. The apparatus according to claim 1, wherein the first set includes no more than 40% of the proximal peaks of the circumferential strut member.

3. The apparatus according to claim 1, wherein, when the stent-graft is unconstrained in the radially-expanded state, for two or more of the circumferential strut members of the self-curving longitudinal portion:

respective first sets of the proximal peaks of the circumferential strut members, which respectively include at least a circumferentially-closest one of the respective proximal peaks to the outermost curve of the self-curving longitudinal portion, and no more than half of the respective proximal peaks of the circumferential strut members, are bent radially inward at least an average angle of 20 degrees toward the central longitudinal axis of the self-curving longitudinal portion, and respective second sets of the proximal peaks of the circumferential strut members, which respectively include all of the respective proximal peaks of the circumferential strut members not in the respective first sets, are not bent radially inward by at least an average angle of 20 degrees toward the central longitudinal axis of the self-curving longitudinal portion.

4. The apparatus according to claim 3, wherein at least two of the two or more of the circumferential strut members are axially adjacent each other along the self-curving longitudinal portion.

5. The apparatus according to claim 3, wherein the circumferential strut members include two end-most circumferential strut members nearest respective axial ends of the self-curving longitudinal portion, and wherein the two or more of the circumferential strut members of the self-curving longitudinal portion are intermediately disposed between the two end-most circumferential strut members.

6. The apparatus according to claim 1,
wherein the self-curving longitudinal portion of the stent-graft comprises:
  a compression-generation spring, which (a) is in an elongated configuration when the stent-graft is in the radially-compressed state, (b) overlaps respective first portions of at least two of the circumferential strut members, and (c) comprises a superelastic alloy; and
  an anti-buckling spring, which (a) overlaps respective second portions of at least two of the circumferential strut members, (b) is shaped so as to define a plurality of curves, and (c) is in fixed orientation with respect to the graft member such that the curves reside substantially in a plane that is substantially parallel to the surface of the graft member, and
wherein the anti-buckling spring and the compression-generation spring are together configured to curve the self-curving longitudinal portion of the stent-graft when the stent-graft is unconstrained in the radially-expanded state, such that a lesser length of the self-curving longitudinal portion of the stent-graft, measured along the innermost curve, is less than 80% of a greater length of the self-curving longitudinal portion of the stent-graft, measured along the outermost curve.

7. The apparatus according to claim 6, wherein the anti-buckling spring is in a substantially relaxed configuration when the stent-graft is unconstrained in the radially-expanded state.

8. The apparatus according to claim 6, wherein the anti-buckling spring is in a longitudinally-compressed configuration when the stent-graft is unconstrained in the radially-expanded state.

9. The apparatus according to claim 6, wherein the anti-buckling spring is sinusoidal or serpentine in the plane that is substantially parallel to the surface of the graft member.

10. The apparatus according to claim 1, wherein, when the stent-graft is unconstrained in the radially-expanded state, for all of the circumferential strut members of the self-curving longitudinal portion:
  respective first sets of the proximal peaks of the circumferential strut members, which respectively include at least a circumferentially-closest one of the respective proximal peaks to the outermost curve of the self-curving longitudinal portion, and no more than half of the respective proximal peaks of the circumferential strut members, are bent radially inward at least an average angle of 20 degrees toward the central longitudinal axis of the self-curving longitudinal portion, and
  respective second sets of the proximal peaks of the circumferential strut members, which respectively include all of the respective proximal peaks of the circumferential strut members not in the respective first sets, are not bent radially inward by at least an average angle of 20 degrees toward the central longitudinal axis of the self-curving longitudinal portion.

11. The apparatus according to claim 1,
wherein two of the circumferential strut members are end-most circumferential strut members nearest respective axial ends of the self-curving longitudinal portion, and
wherein the at least one of the circumferential strut members of the self-curving longitudinal portion is intermediately disposed between the two end-most circumferential strut members.

12. A method for treating a subject, comprising:
transvascularly introducing a generally tubular endovascular self-curving stent-graft into a blood vessel of the subject while the stent-graft is in a radially-compressed delivery state, which stent-graft (1) includes a self-curving longitudinal portion having proximal and distal ends, (2) is configured to transition from the radially-compressed delivery state to a radially-expanded state, wherein, when the stent-graft is unconstrained in the radially-expanded state, the self-curving longitudinal portion of the stent-graft is curved so as to define an innermost curve and an outermost curve, and (3) includes:
  (i) a plurality of circumferential strut members, disposed at respective axial positions along the self-curving longitudinal portion of the stent-graft, surrounding a central longitudinal axis of the self-curving longitudinal portion of the stent-graft, wherein each of the circumferential strut members of the self-curving longitudinal portion is shaped so as to define a plurality of proximal peaks; and
  (ii) a graft member, which includes one or more substantially blood-impervious flexible sheets, and which is fixed to the circumferential strut members;
creating a tight seal between the graft member at the proximal end of the self-curving longitudinal portion of the stent-graft and a wall of the curved blood vessel, by transitioning the stent-graft to the radially-expanded state in the curved blood vessel,
wherein, when the stent-graft is unconstrained in the radially-expanded state, for at least one of the circumferential strut members of the self-curving longitudinal portion:
  a first set of the proximal peaks of the circumferential strut member, which includes at least a circumferentially-closest one of the proximal peaks to the outermost curve of the self-curving longitudinal portion, and no more than half of the proximal peaks of the circumferential strut member, are bent radially inward at least an average angle of 20 degrees toward the central longitudinal axis of the self-curving longitudinal portion, and
  a second set of the proximal peaks of the circumferential strut member, which includes all of the proximal peaks of the circumferential strut member not in the first set, are not bent radially inward by at least an average angle of 20 degrees toward the central longitudinal axis of the self-curving longitudinal portion.

13. The method according to claim 12, wherein the first set includes no more than 40% of the proximal peaks of the circumferential strut member.

14. The method according to claim 12, wherein, when the stent-graft is unconstrained in the radially-expanded state, for two or more of the circumferential strut members of the self-curving longitudinal portion:
  respective first sets of the proximal peaks of the circumferential strut members, which respectively include at least a circumferentially-closest one of the respective proximal peaks to the outermost curve of the self-curving longitudinal portion, and no more than half of the respective proximal peaks of the circumferential strut members, are bent radially inward at least an average angle of 20 degrees toward the central longitudinal axis of the self-curving longitudinal portion, and respective second sets of the proximal peaks of the circumferential strut members, which respectively include all of the respective proximal peaks of the circumferential strut members not in the respective first sets, are not bent radially inward by at least an average angle of 20 degrees toward the central longitudinal axis of the self-curving longitudinal portion.

15. The method according to claim 14, wherein at least two of the two or more of the circumferential strut members are axially adjacent each other along the self-curving longitudinal portion.

16. The method according to claim 14,
wherein the circumferential strut members include two end-most circumferential strut members nearest respective axial ends of the self-curving longitudinal portion, and
wherein the two or more of the circumferential strut members of the self-curving longitudinal portion are intermediately disposed between the two end-most circumferential strut members.

17. The method according to claim 12,
wherein the self-curving longitudinal portion of the stent-graft includes:
a compression-generation spring, which (a) is in an elongated configuration when the stent-graft is in the radially-compressed state, (b) overlaps respective first portions of at least two of the circumferential strut members, and (c) comprises a superelastic alloy; and
an anti-buckling spring, which (a) overlaps respective second portions of at least two of the circumferential strut members, (b) is shaped so as to define a plurality of curves, and (c) is in fixed orientation with respect to the graft member such that the curves reside substantially in a plane that is substantially parallel to the surface of the graft member, and
wherein the anti-buckling spring and the compression-generation spring are together configured to curve the self-curving longitudinal portion of the stent-graft when the stent-graft is unconstrained in the radially-expanded state, such that a lesser length of the self-curving longitudinal portion of the stent-graft, measured along the innermost curve, is less than 80% of a greater length of the self-curving longitudinal portion of the stent-graft, measured along the outermost curve.

18. The method according to claim 17, wherein the anti-buckling spring is in a substantially relaxed configuration when the stent-graft is unconstrained in the radially-expanded state.

19. The method according to claim 17, wherein the anti-buckling spring is in a longitudinally-compressed configuration when the stent-graft is unconstrained in the radially-expanded state.

20. The method according to claim 17, wherein the anti-buckling spring is sinusoidal or serpentine in the plane that is substantially parallel to the surface of the graft member.

21. The method according to claim 12, wherein, when the stent-graft is unconstrained in the radially-expanded state, for all of the circumferential strut members of the self-curving longitudinal portion:

respective first sets of the proximal peaks of the circumferential strut members, which respectively include at least a circumferentially-closest one of the respective proximal peaks to the outermost curve of the self-curving longitudinal portion, and no more than half of the respective proximal peaks of the circumferential strut members, are bent radially inward at least an average angle of 20 degrees toward the central longitudinal axis of the self-curving longitudinal portion, and respective second sets of the proximal peaks of the circumferential strut members, which respectively include all of the respective proximal peaks of the circumferential strut members not in the respective first sets, are not bent radially inward by at least an average angle of 20 degrees toward the central longitudinal axis of the self-curving longitudinal portion.

22. The method according to claim 12,
wherein two of the circumferential strut members are end-most circumferential strut members nearest respective axial ends of the self-curving longitudinal portion, and
wherein the at least one of the circumferential strut members of the self-curving longitudinal portion is intermediately disposed between the two end-most circumferential strut members.

* * * * *